(12) United States Patent
Budiman

(10) Patent No.: US 10,653,836 B2
(45) Date of Patent: *May 19, 2020

(54) SYSTEM FOR MONITORING SAFETY IN MEDICATION DELIVERY FOR DIABETES MANAGEMENT

(71) Applicant: Abbott Diabetes Care Inc., Alameda, CA (US)

(72) Inventor: Erwin S. Budiman, Fremont, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 21 days.

This patent is subject to a terminal disclaimer.

(21) Appl. No.: 15/830,481

(22) Filed: Dec. 4, 2017

(65) Prior Publication Data
US 2018/0154076 A1 Jun. 7, 2018

Related U.S. Application Data

(60) Continuation of application No. 14/528,891, filed on Oct. 30, 2014, now Pat. No. 9,833,571, which is a
(Continued)

(51) Int. Cl.
*A61M 31/00* (2006.01)
*A61K 9/22* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ............ A61B 5/14532; A61B 5/4839; A61M 2005/14208; A61M 2005/14296; A61M 2205/17; A61M 2205/3303; A61M 2205/3569; A61M 2205/50; A61M 2205/52; A61M 2205/702; A61M 2230/201; A61M 5/142; A61M 5/1723; G06F 19/3468
(Continued)

(56) References Cited

U.S. PATENT DOCUMENTS 5,822,715 A 10/1998 Worthington et al.
2005/0027463 A1 2/2005 Goode et al.
(Continued)

*Primary Examiner* — Jason E Flick
(74) *Attorney, Agent, or Firm* — Vorys, Sater, Seymour and Pease LLP

(57) ABSTRACT

An integrated diabetes management (IDM) system includes a safety layer which, in one configuration has two components, one located between a glucose sensor and a controller and a second component located between a controller and a pump, to monitor various aspects of signals and modify those signals for compatibility and safety purposes. In one application, the safety layer receives output control signals from a controller and modifies those control signals as a function of an actual amount of insulin delivered to the user. The safety layer allows for an increased level of safety in the IDM system and permits development of separate hardware and software upgrades with the safety layer assuring that compatibility between components will continue.

20 Claims, 6 Drawing Sheets

Related U.S. Application Data continuation of application No. 14/177,122, filed on Feb. 10, 2014, now Pat. No. 8,876,803, which is a continuation of application No. 13/645,233, filed on Oct. 4, 2012, now Pat. No. 8,647,321, which is a division of application No. 12/785,096, filed on May 21, 2010, now Pat. No. 8,398,616.

(60) Provisional application No. 61/180,774, filed on May 22, 2009.

(51) Int. Cl.
| | | |
|---|---|---|
| *A61M 5/172* | (2006.01) | |
| *A61B 5/145* | (2006.01) | |
| *A61B 5/00* | (2006.01) | |
| *A61M 5/142* | (2006.01) | |
| *G06F 19/00* | (2018.01) | |
| *G16H 50/20* | (2018.01) | |

(52) U.S. Cl.
CPC ......... *A61M 5/142* (2013.01); *G06F 19/3468* (2013.01); *G16H 50/20* (2018.01); *A61M 2005/14208* (2013.01); *A61M 2005/14296* (2013.01); *A61M 2205/17* (2013.01); *A61M 2205/3303* (2013.01); *A61M 2205/3569* (2013.01); *A61M 2205/50* (2013.01); *A61M 2205/52* (2013.01); *A61M 2205/702* (2013.01); *A61M 2230/201* (2013.01)

(58) Field of Classification Search
USPC .......................................................... 604/504
See application file for complete search history.

(56) References Cited

U.S. PATENT DOCUMENTS

| | | |
|---|---|---|
| 2007/0078314 A1 | 4/2007 | Grounsell et al. |
| 2007/0173761 A1 | 7/2007 | Kanderian, Jr. et al. |
| 2009/0105636 A1* | 4/2009 | Hayter ................ A61M 5/1723 604/66 |

\* cited by examiner

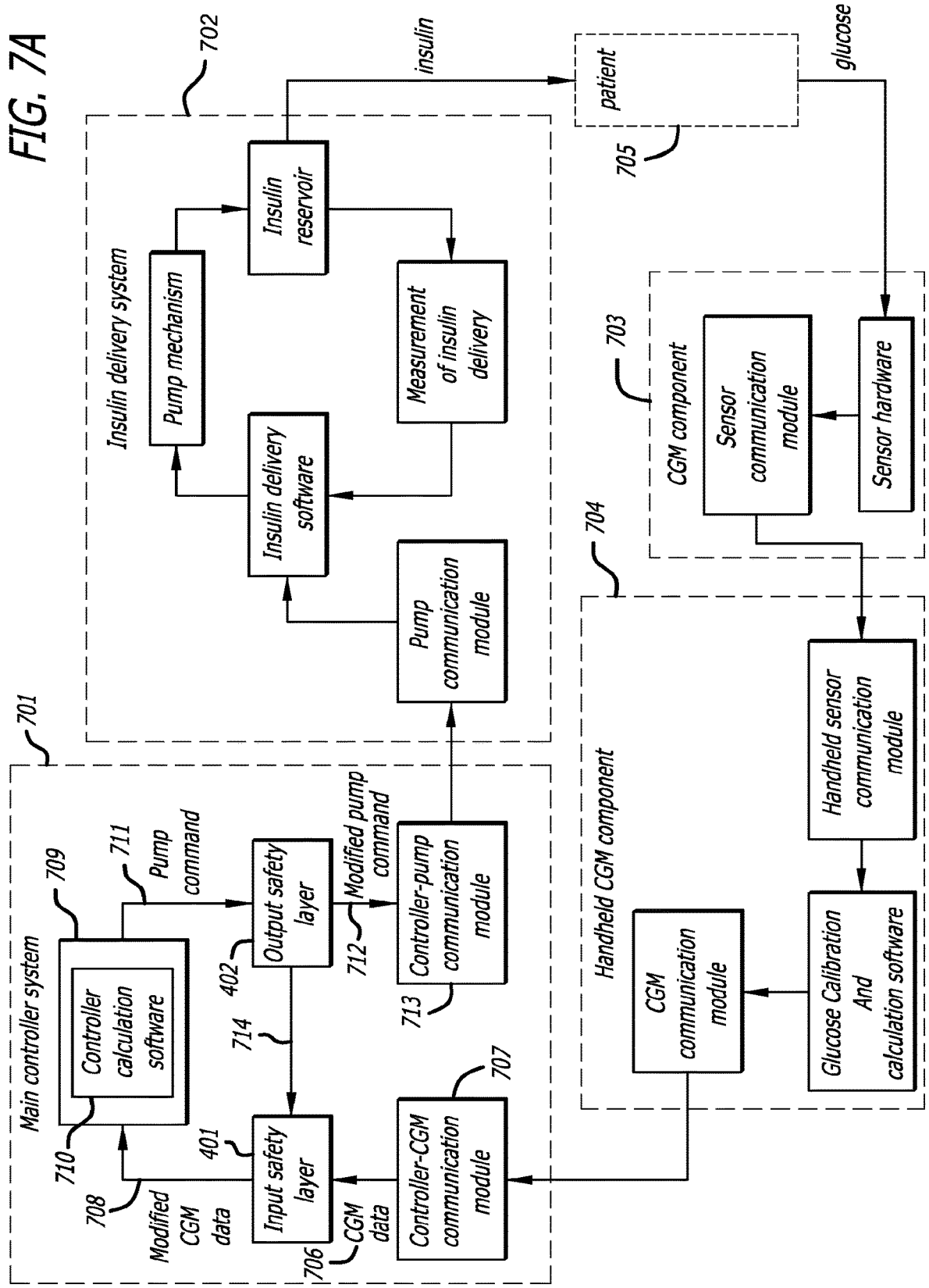

SYSTEM FOR MONITORING SAFETY IN MEDICATION DELIVERY FOR DIABETES MANAGEMENT

CROSS-REFERENCE TO RELATED APPLICATIONS

This application is a continuation of application Ser. No. 14/177,122 filed Feb. 10, 2014, now U.S. Pat. No. 8,876, 803, which is a continuation of application Ser. No. 13/645, 233 filed Oct. 4, 2012, now U.S. Pat. No. 8,647,321, which is a divisional of Ser. No. 12/785,096 filed May 21, 2010, now U.S. Pat. No. 8,398,616, which claims the benefit of U.S. Application No. 61/180,774, filed May 22, 2009, all of which are incorporated herein by reference in their entireties for all purposes.

This application is also related to U.S. application Ser. No. 12/785,104 entitled "Safety Features For Integrated Insulin Delivery System," (U.S. Provisional Application No. 61/180,627, filed May 22, 2009), now U.S. Pat. No. 8,257, 300; U.S. application Ser. No. 12/785,144 entitled "Usability Features For Integrated Insulin Delivery System," (U.S. Provisional Application No. 61/180,649, filed May 22, 2009), now U.S. Pat. No. 8,597,274; U.S. application Ser. No. 12/785,196 entitled "Adaptive Insulin Delivery System," (U.S. Provisional Application No. 61/180,767, filed May 22, 2009; and U.S. application Ser. No. 12/784,981 entitled "Methods for Reducing False Hypoglycemia Alarm Occurrence," (U.S. Provisional Application No. 61/180,700, filed May 22, 2009).

BACKGROUND

The invention is generally related to systems and methods for control over the delivery of medication and more particularly, to a safety system for monitoring and controlling the delivery of medication.

Diabetes is a metabolic disorder that afflicts tens of millions of people throughout the world. Diabetes results from the inability of the body to properly utilize and metabolize carbohydrates, particularly glucose. Normally, the finely-tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In patients with insulin-dependent diabetes, the symptoms of the disease can be controlled by administering additional insulin (or other agents that have similar effects) by injection or by external or implantable insulin pumps. It is understood that throughout this document, the terms "patient" and "user" are used interchangeably. The "correct" insulin dosage is a function of the level of glucose in the blood. Ideally, insulin administration should be continuously readjusted in response to changes in glucose level.

Presently, systems are available for monitoring glucose levels by implanting a glucose sensitive probe into the user. Such probes measure various properties of blood or other tissues, including optical absorption, electrochemical potential and enzymatic products. The output of such sensors can be communicated to a hand held device that is used to calculate an appropriate dosage of insulin to be delivered into the blood stream in view of several factors, such as a user's present glucose level, insulin usage rate, carbohydrates consumed or to be consumed and exercise, among others. These calculations can then be used to control a pump that delivers the insulin, either at a controlled "basal" rate, or as a "bolus." When provided as an integrated system, a continuous glucose monitor ("CGM"), a pump, and a control means work together to provide continuous glucose monitoring and insulin pump control. The components of integrated diabetes management ("IDM") systems, whether implemented as a fully closed-loop, semi closed-loop, or an open loop system must be tightly integrated to insure the accuracy of the glucose monitor and to protect the user from either under- or over-dosage of insulin, as well as improved usability, control, and safety of the system.

Not all components are likely to be made by a single developer or be based on a universal design platform, and users have always tended to mix and match components to suit their individual needs. In the case of a development platform for these systems, it is likely that both outside-designed (third-party) controller modules as well as insider-developed systems and platforms may evolve over time, and more than one version may exist at any given time. While modern trends often promote hardware and software compatibility, when mixing components created by different designers or manufacturers, one must consider the careful design of hazard mitigation features, such as the safety limits of such critical life-saving devices and components. As hardware and software components get replaced or improved, it is possible that many aspects of hazard mitigation becomes so coupled with the particular configurations of a particular case, that a careful redesign may be necessary to account for the new changes. Moreover, it is anticipated that system and value constraints can change due to component hardware and software upgrades over the life of a closed loop or semi-closed loop diabetes control system.

Under normal operating conditions, a fully autonomous closed loop system is in full control of its insulin command calculation. This implies that while closed loop is in effect, the user may be denied access to some of the system's functionality such as the ability to deliver a bolus. While, in some instances, this may have been designed from a safety perspective, the user may perceive such features to inhibit control over the ability to self-medicate or limit control over the device. Consequently, a closed loop or semi-closed loop system should be able to account for the effects of a user-initiated command such as a meal bolus, even if it is not necessarily accompanied with meal content information. Yet, the requirement to allow such user intervention could cause a momentary violation of pump delivery limits set by designers, even if the control system (without the addition of the invention herein disclosed) was designed not to generate autonomous commands that exceed the same pump delivery limits.

What has been needed, and heretofore unavailable, is an integrated, automated system combining continuous glucose monitoring and controlled insulin delivery that provides modularity for rapid development of system components by different designers, and that bestows an increased sense of freedom to the user, such as the ability to self-medicate in conjunction with a closed-loop system, all while providing for safety in the accurate delivery of insulin.

SUMMARY

The invention is directed to a safety layer for an integrated diabetes management system. In one aspect, there is provided an integrated diabetes management system comprising a glucose sensor configured to provide sensor glucose data representative of sensed glucose, a delivery device configured to deliver medication in response to a delivery control signal, a controller programmed to receive glucose data and to provide an output control signal as a function of the received glucose data; and a safety layer programmed to receive at least one of the sensor glucose data and the output control signal, and to modify at least one of the sensor glucose data and the output control signal; wherein the glucose data would be modified to become modified glucose data; and wherein the output control signal would be modified to become a modified output control signal that would be provided as the delivery control signal.

In more detailed aspects, the safety layer is further programmed to monitor the amount of medication delivered and to modify the output control signal at least partially as a function of the monitored amount of medication delivered, wherein the amount of medication delivered monitored by the safety layer comprises insulin on board. Additionally, the safety layer is further programmed to modify at least one of the glucose data and the output control signal in accordance with a characteristic of at least one of the glucose sensor and the delivery device. Further, the safety layer is programmed to modify the sensor glucose data as a function of delivery device output, and the safety layer is programmed to modify the output control signal as a function of delivery device output.

In other aspects, the integrated diabetes management system further comprises a communication module, wherein the controller comprises a controller calculation software module configured to provide the output control signal and wherein the communication module is configured to provide the delivery control signal to the delivery device, wherein the safety layer is configured to intercept the output control signal and substitute the modified control signal to the communication module without any reconfiguration of the communication module or the controller calculation software module. Additionally, the controller comprises a controller calculation software module configured to receive glucose data and provide the output control signal, and the safety layer is configured to intercept the sensor glucose data from the glucose sensor and substitute the modified glucose data to the controller calculation software module without any reconfiguration of the glucose sensor or the controller calculation software module.

In yet more detailed aspects, the delivery device has a maximum delivery rate, and the safety layer is further programmed to determine the maximum delivery rate of the delivery device, determine the amount of medication to be delivered by the output control signal, and if the output control signal is configured for a higher delivery rate than the maximum delivery rate of the delivery device, the safety layer calculates a modified delivery rate and schedule based at least in part on the maximum delivery rate of the delivery device to achieve delivery of the same amount of medication as configured by the output control signal. Further, the safety layer is further programmed to taper the modified delivery rate over the delivery schedule. The safety layer is further programmed to display the modified delivery rate and the delivery schedule.

In another aspect, the glucose sensor includes an output having a first range representative of glucose levels, the controller has an input having a second range representative of glucose levels, wherein the second range is different from the first range, and the safety layer is configured to receive glucose data from the glucose sensor, modify the received glucose data for compatibility with the second range, and substitute the modified glucose data to the input of the controller.

In a related aspect, the glucose sensor provides glucose data having a first format, and the controller is configured to receive glucose data having a second format, the safety layer is further programmed to determine if the first format and the second format are equivalent, if the first and second data formats are not equivalent, the safety layer is programmed to modify the glucose data signals to the second format and substitute the modified glucose signals to the controller.

In other detailed aspects, the safety layer further comprises an input safety module operably connected to the glucose sensor, and an output safety module operably connected to the medication delivery device, wherein the output safety module provides feedback to the input safety module. Further, the feedback comprises a function of a limit on the delivery device and the modified control signal and wherein the modified glucose data is further determined as a function of the feedback. Also, the delivery control signal is representative of a required medication amount for delivery, wherein the safety layer determines a maximum delivery rate of the medication delivery device and is configured to calculate a delivery schedule as a factor of the maximum delivery rate and the required medication amount, the required medication amount being determined at least partially by the sensed glucose.

In yet further aspects, the integrated diabetes management system further comprises a memory module, and an input, wherein the safety layer is configured to store the required medication amount in the memory and update the required medication amount according to a remaining delivery schedule, the modified output control signal, and a delivery command received at the input. In a further aspect, the delivery schedule is a tapered delivery of insulin.

In much more detailed aspects, the safety layer is further programmed to provide the modified control signal such that it conforms to a current-driven hardware standard. The safety layer is further programmed to provide the modified control signal such that it conforms to a voltage-driven hardware standard.

In method aspects according to the invention, there is provided a method of diabetes management comprising sensing glucose and providing sensor glucose data representative of sensed glucose, delivering medication in response to a delivery control signal, receiving glucose data and providing an output control signal as a function of the received glucose data, monitoring the amount of medication delivered, and receiving at least one of the sensor glucose data and the output control signal, and modifying at least one of the sensor glucose data and the output control signal, wherein the glucose data would be modified to become modified glucose data, wherein the output control signal would be modified to become a modified output control signal, communicating the modified output control signal as the delivery control signal, and wherein modifying at least one of the glucose data and the output control signal includes modifying as a function of the monitored amount of medication delivered.

In more detailed aspects, there is provided calculating the output control signal, and intercepting the output control signal and substituting the modified control signal as the delivery control signal without reconfiguring the step of calculating the output control signal or the step of communicating a delivery control signal. Additionally, aspects further comprise safety monitoring the sensor glucose data between the steps of providing sensor glucose data and receiving glucose data, and separately safety monitoring the output control signal. Additionally the step of separately safety monitoring the output control signal further comprises also providing feedback to the safety monitoring of the sensor glucose data step. The step of providing feedback comprises providing feedback as a function of a limit on the delivery of medication and on the modified output control signal, and wherein the step of modifying glucose data further includes modifying glucose data as a function of the feedback.

The features and advantages of the invention will be more readily understood from the following detailed description which should be read in conjunction with the accompanying drawings.

BRIEF DESCRIPTION OF THE FIGURES

FIGS. 7A and 7B depict a schematic diagram of the components of an IDM system, including an embodiment of a safety layer, with FIG. 7A showing an entire system having a main controller system, an insulin delivery system, a continuous glucose monitor (CGM) component, and a handheld CGM component showing safety layers in the main controller system, and with FIG. 7B showing a main handheld system with safety layers.

DETAILED DESCRIPTION OF THE PREFERRED EMBODIMENTS

For the purposes of promoting an understanding of the principles of the invention, reference will now be made to a number of illustrative embodiments shown in the attached drawings and specific language will be used to describe the same.

Figure 1:
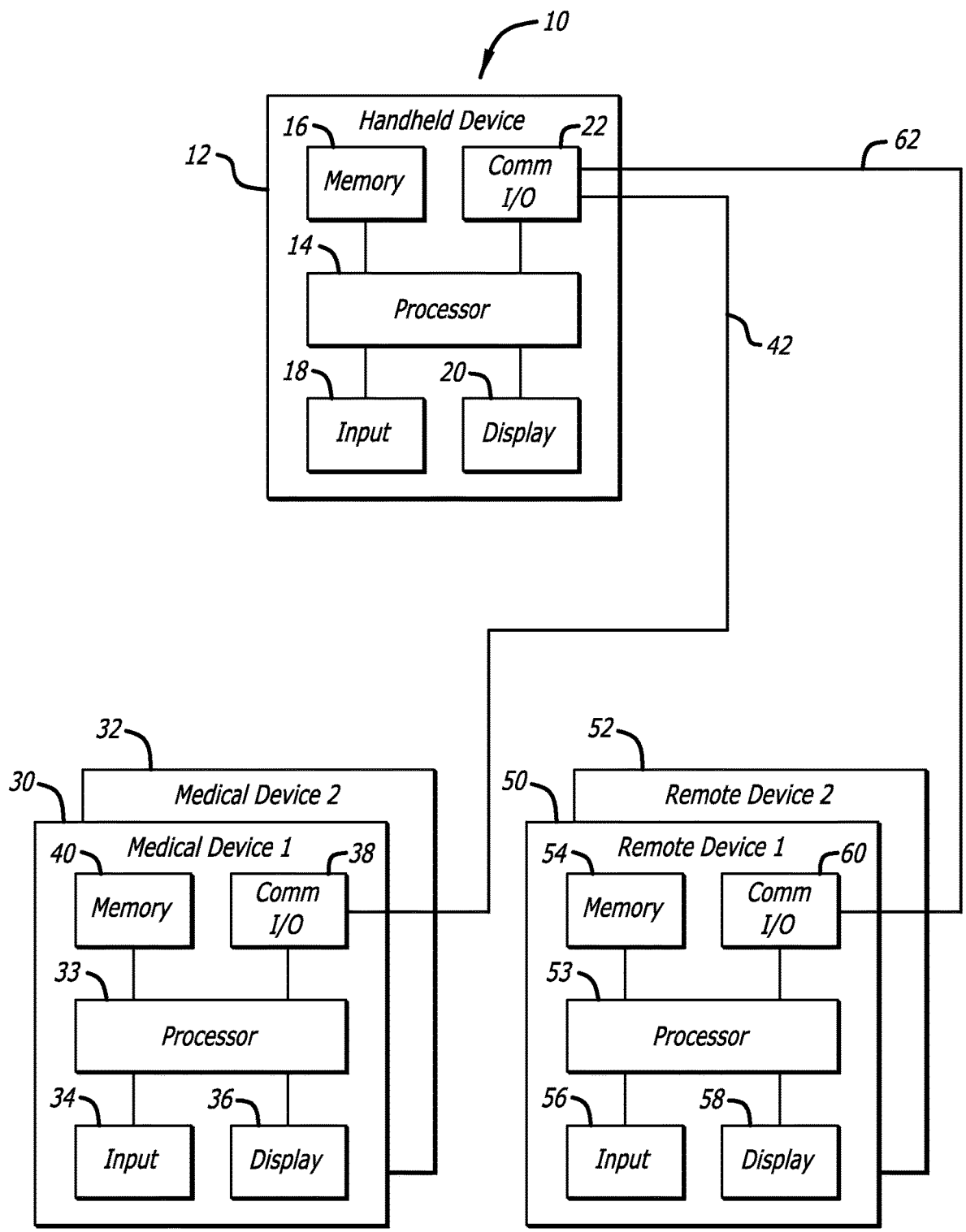
FIG. 1 is a schematic diagram illustrating an exemplary embodiment of an electronic device and its various components in operable communication with one or more medical devices, such as a glucose monitor or drug delivery pump, and optionally, in operable communication with a remote computing device.

Referring now to FIG. 1, a block diagram of one illustrative embodiment of a system 10 for monitoring, determining and/or providing drug administration information is shown. It should be understood for the purpose of the depicted embodiments that system 10 is depicted as an IDM system including a CGM sensor device, an insulin pump, and a control means (for example, a handheld device) that may work together to provide continuous glucose monitoring and insulin pump control, and that may further be implemented as a fully closed-loop, semi closed-loop, or an open loop system. In the illustrated embodiment, the system 10 includes an electronic device 12 having a processor 14 in data communication with a memory unit 16, an input device 18, a display 20, and a communication input/output unit 22. The electronic device 12, which may be handheld, may be provided in the form of a general purpose computer, central server, personal computer (PC), laptop or notebook computer, personal data assistant (PDA) or other hand-held device, external infusion pump, glucose meter, analyte sensing system, or the like. The electronic device 12 may be configured to operate in accordance with one or more operating systems including for example, but not limited to, WINDOWS, Unix, LINUX, BSD, SOLARIS, MAC OS, or, an embedded OS such as ANDROID, PALM OS, WEBOS, eCOS, QNX, or WINCE, and may be configured to process data according to one or more internet protocols for example, but not limited to, NetBios, TCP/IP and APPLE-TALK. The processor 14 is microprocessor-based, although the processor 14 may be formed of one or more general purpose and/or application specific circuits and operable as described hereinafter. The memory unit 16 includes sufficient capacity to store operational data, one or more software algorithms executable by the processor 14, and other user inputted data. The memory unit 16 may include one or more memory or other data storage devices.

Display 20 is also included for viewing information relating to operation of the device 12 and/or system 10. Such a display may be a display device including for example, but not limited to, a light emitting diode (LED) display, a liquid crystal display (LCD), a cathode ray tube (CRT) display, or the like. Additionally, display 20 may include an audible display configured to communicate information to a user, another person, or another electronic system having audio recognition capabilities via one or more coded patterns, vibrations, synthesized voice responses, or the like. Additionally, display 20 may include one or more tactile indicators configured to display tactile information that may be discerned by the user or another person.

Input device 18 may be used in a manner to input and/or modify data. Input device 18 may include a keyboard or keypad for entering alphanumeric data into the processor 14. Such a keyboard or keypad may include one or more keys or buttons configured with one or more tactile indicators to allow users with poor eyesight to find and select an appropriate one or more of the keys, and/or to allow users to find and select an appropriate one or more of the keys in poor lighting conditions. Additionally, input device 18 may include a mouse or other point and click device for selecting information presented on the display 20. Additionally, input device 18 may include display 20, configured as a touch screen graphical user interface. In this embodiment, the display 20 includes one or more selectable inputs that a user may select by touching an appropriate portion of the display 20 using an appropriate implement.

Input device 18 may also include a number of switches or buttons that may be activated by a user to select corresponding operational features of the device 12 and/or system 10. Input device 18 may also be or include voice-activated circuitry responsive to voice commands to provide corresponding input data to the processor 14. The input device 18 and/or display 20 may be included with or separate from the electronic device 12.

System 10 may also include a number of medical devices 30, 32 which carry out various functions, for example, but not limited to, monitoring, sensing, diagnostic, communication and treatment functions. In such embodiments, any of the one or more of the medical devices 30, 32 may be implanted within the user's body, coupled externally to the user's body (for example, such as an infusion pump), or separate from the user's body. In some embodiments, medical devices 30, 32 are controlled remotely by electronic device 12. Additionally, one or more of the medical devices may be mounted to and/or form part of the electronic device 12. For example, in some embodiments, electronic device 12 includes an integrated glucose meter or strip port and is configured to receive a signal representative of a glucose value and display the value to a user. Electronic device 12 may further be configured to be used to calibrate a continuous glucose monitor (CGM) or for calculating insulin amounts for bolus delivery. Typically, the medical devices 30, 32 are each configured to communicate wirelessly with the communication I/O unit 22 of the electronic device 12 via one of a corresponding number of wireless communication links. Wireless communication is preferable when medical device 30, 32 is configured to be located on a remote part of the body, for example, in an embodiment wherein medical device 30, 32 is a continuous glucose monitor (CGM) or sensor, or insulin pump, worn under clothing.

Electronic device 12 communicates with medical device 30, 32 via a wireless protocol, or, in some embodiments, is directly connected via a wire. The wireless communications between the various components of the system 10 may be one-way or two-way. The form of wireless communication used may include, but should not be limited to, radio frequency (RF) communication, infrared (IR) communication, Wi-Fi, RFID (inductive coupling) communication, acoustic communication, capacitive signaling (through a conductive body), galvanic signaling (through a conductive body), BLUETOOTH, or the like. Electronic device 12 and each of the medical devices 30, 32 include circuitry for conducting such wireless communications circuit. In another embodiment, one or more of the medical devices 30, 32 may be configured to communicate with electronic device 12 via one or more serial or parallel configured hardwire connections therebetween.

Each of the one or more medical devices 30, 32 may include one or more of a processing unit 33, input 34 or output 36 circuitry and/or devices, communication ports 38, and/or one or more suitable data and/or program storage devices 40. It may be understood that not all medical devices 30, 32 will have the same componentry, but rather will only have the components necessary to carry out the designed function of the medical device. For example, in one embodiment, a medical device 30, 32 may be capable of integration with electronic device 12 and thus omit input 34, display 36, and/or processor 33. In another embodiment, medical device 30, 32 is capable of stand-alone operation, and is further configured to function as electronic device 12, should communication with electronic device 12 be interrupted. In another embodiment, medical device 30, 32 may include processor, memory and communication capability, but does not have an input 34 or a display 36. In still another embodiment, the medical device 30, 32 may include an input 34, but lack a display 36.

In some embodiments, the system 10 may additionally include a remote devices 50, 52. The remote device 50, 52 may include a processor 53, which may be identical or similar to the processor 33 or processor 14, a memory or other data storage unit 54, a input device 56, which may include any one or more of the input devices described hereinabove, a display unit 58 which may include any one or more of the display units described hereinabove, and a communication I/O circuitry 60. The remote device 50, 52 may be configured to communicate with the electronic device 12 or medical devices(s) 30, 32 via any wired or wireless communication interface 62, which may include any of the communication interfaces or links described hereinabove. Although not specifically shown, remote device 50, 52 may also be configured to communicate directly with one or more medical devices 30, 32, instead of communicating with the medical device through electronic device 12.

System 10 may be provided in any of a variety of configurations, and examples of some such configurations will now be described. It will be understood, however, that the following examples are provided merely for illustrative purposes, and should not be considered limiting in any way. Those skilled in the art may recognize other possible implementations of a fully closed-loop, semi closed-loop, or open loop diabetes control arrangement, and any such other implementations are contemplated by this disclosure.

In a first exemplary implementation of the system 10, the medical device 30, 32 is provided in the form of one or more sensors 31 (FIG. 2) or sensing systems that are external to the user's body and/or sensor techniques for providing information relating to the physiological condition of the user. Examples of such sensors or sensing systems may include, but should not be limited to, a glucose strip sensor/meter, a body temperature sensor, a blood pressure sensor, a heart rate sensor, one or more bio-markers configured to capture one or more physiological states of the body, for example, HBA1C, or the like. In implementations that include a glucose sensor, system 10 may be a fully closed-loop system operable in a manner to automatically monitor glucose and deliver insulin, as appropriate, to maintain glucose at desired levels. Information provided by any such sensors and/or sensor techniques may be communicated by system 10 using any one or more wired or wireless communication techniques.

The various medical devices 30, 32 may additionally include an insulin pump 35 (FIG. 2) configured to be worn externally to the user's body and also configured to controllably deliver insulin to the user's body. In one such embodiment, medical devices 30, 32 include at least one implantable or externally worn drug pump. In one embodiment, an insulin pump is configured to controllably deliver insulin to the user's body. In this embodiment, the insulin pump is also configured to wirelessly transmit information relating to insulin delivery to the handheld device 12. The handheld device 12 is configured to monitor insulin delivery by the pump, and may further be configured to determine and recommend insulin bolus amounts, carbohydrate intake, exercise, and the like to the user. The system 10 may be configured in this embodiment to provide for transmission of wireless information from the handheld device 12 to the insulin pump.

Figure 2:
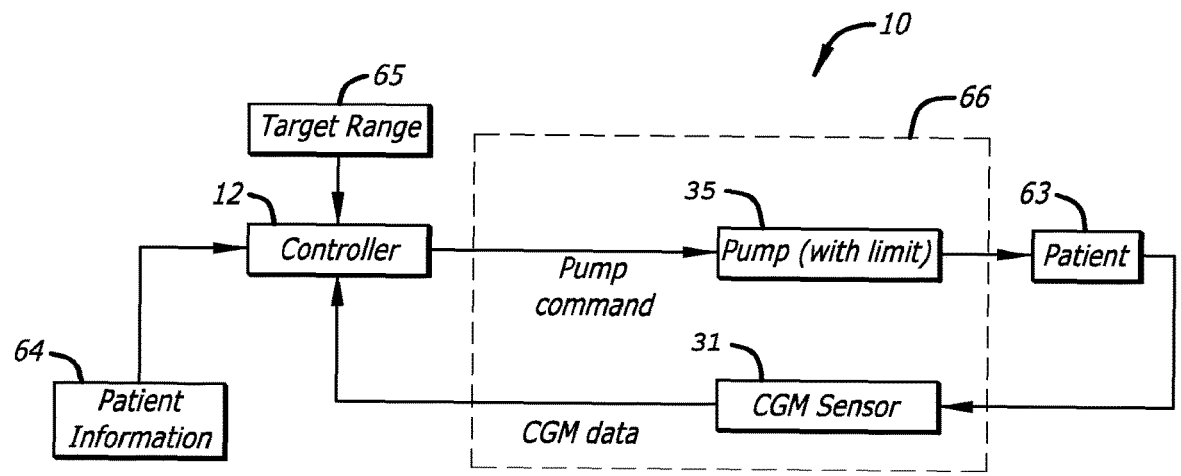
FIG. 2 depicts an integrated diabetes management ("IDM") system in accordance with aspects of the present invention.

In an implementation of the system 10, the electronic device 12 is provided in the form of a handheld device, such as a PDA or other handheld device. In a further embodiment, the handheld device 12 is configured to control insulin delivery to the user by determining insulin delivery commands and transmitting such commands to an insulin pump 35 (FIG. 2). The insulin pump, in turn, is configured to receive the insulin delivery commands from the handheld device 12, and to deliver insulin to the user according to the commands. The insulin pump, in this embodiment, may further process the insulin pump commands provided by the handheld unit 12. The system 10 will typically be configured in this embodiment to provide for transmission of wireless information from the insulin pump back to the handheld device 12 to thereby allow for monitoring of pump operation. The system 10 may further include one or more implanted and/or external sensors of the type described in the previous example.

Those skilled in the art will recognize other possible implementations of a fully closed-loop, semi closed-loop, or open loop diabetes control arrangement using at least some of the components of the system 10 illustrated in FIG. 1. For example, the electronic device 12 in one or more of the above examples may be provided in the form of a PDA, laptop, notebook or personal computer configured to communicate with one or more of the medical devices 30, 32, at least one of which is an insulin delivery system, to monitor and/or control the delivery of insulin to the user. In further embodiments, electronic device may include a communication port 22 in the form of a BLUETOOTH or other wireless transmitter/receiver, serial port or USB port, or other custom configured serial data communication port. In some embodiments, remote device 50, 52 is configured to communicate with the electronic device 12 and/or one or more of the medical devices 30, 32, to control and/or monitor insulin delivery to the user, and/or to transfer one or more software programs and/or data to the electronic device 12. Remote device 50, 52 may take the form of a PC, PDA, laptop or notebook computer, handheld or otherwise portable device, and may reside in a caregiver's office or other remote location. In the various embodiments, communication between the remote device and any component of the system 10 may be accomplished via an intranet, internet (for example, world-wide-web), cellular, telephone modem, RF, USB connection cable, or other communication link 62. Any one or more internet protocols may be used in such communications. Additionally, any mobile content delivery system; for example, Wi-Fi, WiMAX, BLUETOOTH, short message system (SMS), or other message scheme may be used to provide for communication between devices comprising the system 10.

FIG. 2 illustrates the components, and operation and control flow, of a closed-loop system. In the depicted embodiment, the system generally includes a sensor and a pump, and a controller module for receiving input from the sensor and for controlling the pump. The term "controller module" as used herein is defined as a hardware device that receives a signal representative of a glucose (for example, from a sensor) and produces signals to control an insulin delivery device (for example, a pump). In some embodiments, the controller module is part of or includes electronic device 12. In some embodiments, electronic device 12 (or handheld controller 12) is part of or includes the controller module. Thus, the controller module may be depicted in the drawings as either a controller or an electronic device 12, and the terms handheld controller, electronic device, controller module, electronic device, and handheld device, are used herein interchangeably. In some embodiments, the controller module is hardware included with or interconnected to electronic device 12. In further embodiments, the controller module is hardware included with or interconnected to sensor 31 and/or pump 35.

In some embodiments, the sensor and/or pump is part of, or includes medical device 30, 32 (that is, medical device 30, 32 can be a pump or a sensor). In some embodiments, the controller module may be part of, or be integrated with, a sensor 31 or a pump 35, or other medical devices 30, 32. Handheld controller 12 preferably has a user interface screen 20 to display information to the user and to request from the user the input of parameters and/or commands. Handheld controller 12 may further comprise a processor 14, and an input means 18, such as buttons or a touch screen, for the user to input and/or set parameters and commands to the system.

Handheld controller 12 includes a memory means 16 configured to store parameters and one or more algorithms that may be executed by processor 14. For example, memory means 16 may store one or more predetermined parameters or algorithms to evaluate glucose data, trends in that data, and future prediction models. A user may also input parameters using input 18 to provide user-specific algorithms such as pumping patterns or algorithms for determining an amount of drug (that is, insulin) to be delivered by an insulin delivery device (IDD), pump 35. Input 18 may also be used to send commands or to bring up a menu of commands for the user to choose from. In some embodiments, these components (that is, input, processor, and memory) comprise the control module. The information may be displayed, for example, on display 20 of handheld controller 12, and user input may be received via input 18. In one embodiment, handheld controller 12 takes into account for both deliveries commanded by the controller as well as deliveries commanded by human input intended to correct or compensate for specific aspects not necessarily known to the controller. The components of the IDM system may cooperatively work together as a single device or separate physical devices.

In one embodiment, handheld controller 12 is provided to allow the user to view via graphical display 20 his or her glucose levels and/or trends and to control the pump 35. Handheld controller 12 sends commands to operate pump 35, such as an automatic insulin basal rate or bolus amount. Handheld controller 12 may automatically send commands based on input from sensor 31 or may send commands after receiving user input via input 18 or input 34 on medical device 30, 32. In at least one embodiment, handheld controller 12 analyzes data from sensor 31 and/or pump 35, and/or communicates data and commands to them. In one embodiment, handheld controller 12 automatically sends the commands to pump 35 based on a sensor reading. Handheld controller 12 may also send commands to direct the pumping action of the pump 35. Handheld controller 12 sends and receives data to and from sensor 31 over a wired connection or wireless communication protocol 42. In another embodiment, data based on the reading is first provided to handheld controller 12 which analyzes the data and presents information to a user or a health care provider (for example, using remote device 50, 52), wherein human input is required to generate the command. For example, handheld controller 12 may request an acknowledgment or feedback from the user before sending the commands, allowing the user to intervene in command selection or transmission. In a further embodiment, handheld controller 12 merely sends alerts or warnings to the user and allows the user to manually select and send the commands via the input 18 of handheld controller 12. In yet another embodiment handheld controller 12 manages commands originated by the control algorithm with or without user approval or intervention, and commands initiated by the user are independent of the control algorithm. The purpose of handheld controller 12 is to process sensor data in real-time and determine whether the glucose levels in a user are too high or too low, and to provide a prediction of future glucose levels based upon sensor readings and the current basal rate and/or recent bolus injections.

In some embodiments, handheld controller 12 includes a means for calibrating the system, including, inputting at the device a finger stick glucose measurement or taking an actual blood sample to obtain a glucose measurement. The device may be integrated with a strip port so that a user may use the strip port to take a manual glucose reading. The strip port includes a known calibration and is configured to take a blood reading to provide a value representative of a glucose. The reading provided from the strip port is internally received at handheld controller 12 and compared to a value from sensor 31 to configure and/or calibrate the system.

Sensor 31 is configured to read a glucose level of a user and to send the reading to be analyzed by handheld controller 12. In some embodiments, sensor 31 is a glucose monitor with a strip port for manually receiving a blood sample. In the depicted embodiments, sensor 31 is a continuous glucose monitoring (CGM) sensor that pierces and/or is held in place at the surface of a user's skin to continuously monitor glucose levels in a user. In an embodiment, CGM sensor 31 (a portable medical device 30, 32) is attached to the surface of a user's skin and includes a small sensor device that at least partially pierces the user's skin and is located in the dermis to be in contact with the interstitial fluid. The sensor device may also be held in place at the skin by a flexible patch. Accordingly, CGM sensor 31 may provide continuous monitoring of user glucose levels. The analyte monitoring system may also include a transmitter and/or receiver for transmitting sensor data to a separate device (for example, pump 35 or handheld electronic device 12). In some embodiments, CGM sensor 31 is in the form of a skin-mounted unit on a user's arm.

In the depicted embodiments, an insulin device or pump 35 delivers insulin to the user through a small tube and cannula (also known as the "infusion set") percutaneously inserted into the user's body. Insulin pump 35 may be in the form of a medical pump, a small portable device (similar to a pager) worn on a belt or placed in a pocket, or it may be in the form of a patch pump that is affixed to the user's skin. In one embodiment, pump 35 is attached to the body by an adhesive patch and is normally worn under clothes. Pump 35 is preferably worn on the skin, includes a power supply, and is relatively small and of a low profile so that it can be hidden from view in a pocket or attached to the skin under clothing.

The pump has disposable and non-disposable components. The disposable components include the reservoir and cannula and (optional) adhesive patch. The non-disposable/reusable component includes the pumping electronics, transmitter and/or receiver, and pump mechanics (not shown). Pump 35 and cannula may be part of the same physical device or comprise separate modules. Pump 35 may also comprise a transmitter and/or receiver for transmitting and/or receiving a signal via connection 42 from handheld controller 12 so that it can be controlled remotely and can report pump-specific data to a remote location.

When provided as an integrated system, the components of system 10 work together to provide real-time continuous glucose monitoring and control of an insulin pump and to allow a user to take immediate corrective or preventative action when glucose levels are either too high or too low. Because pump 35 and sensor 31 are miniaturized they may have very limited control panels, if any at all, and thus, in some embodiments, sensor 31, pump 35, and controller 12 may all be integrated into a single device. In other embodiments, sensor 31, pump 35, and controller 12 may be organized as two or three separate components. The components may be in wired communication, radio communication, fluid connection, or other communication protocol suitable for sending and receiving information between the components. Some components may be constructed to be reusable while others are disposable. For example, the cannula and the sensor may be disposable pieces apart from the pump 35 and CGM sensor 31 which are both preferably reusable. The cannula and/or sensor will preferably be in fluid isolation from other components. Each component may have modular fittings so that the disposable components may interact with the non-disposable components while remaining in fluid isolation from each other.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's glucose level and administering insulin or other glucose-altering drug, for example, glucose lowering or raising drug, as needed to maintain the person's glucose within desired ranges. In any of the above examples, the system 10 is thus configured to determine, based on some amount of user-specific information, an appropriate amount, type and/or timing of insulin or other glucose-altering drug to administer in order to maintain normal glucose levels without causing hypoglycemia or hyperglycemia.

In some embodiments, the system 10 is configured in a manner to control one or more external (for example, subcutaneous, transcutaneous or transdermal) and/or implanted insulin pumps to automatically infuse or otherwise supply the appropriate amount and type of insulin to the user's body in the form of one or more insulin boluses. Such insulin bolus administration information may be or include, for example, insulin bolus quantity or quantities, bolus type, insulin bolus delivery time, times or intervals (for example, single delivery, multiple discrete deliveries, continuous delivery, etc.), and the like. Examples of user supplied information may be, for example but not limited to, user glucose concentration, information relating to a meal or snack that has been ingested, is being ingested, or is to be ingested sometime in the future, user exercise information, user stress information, user illness information, information relating to the user's menstrual cycle, and the like.

System 10 may also include a delivery mechanism for delivering controlled amounts of a drug; for example, insulin, glucagon, incretin, or the like to pump 35, and/or offering an actionable therapy recommendation to the user via the display 20, for example, ingesting carbohydrates, exercising, etc. In other embodiments, the system 10 is configured in a manner to display or otherwise notify the user of the appropriate amount, type, and/or timing of insulin in the form of an insulin recommendation. In such embodiments, hardware and/or software forming part of the system 10 allows the user to accept the recommended insulin amount, type, and/or timing, or to reject it. If accepted, the system 10, in one embodiment, automatically infuses or otherwise provides the appropriate amount and type of insulin to the user's body in the form of one or more insulin boluses. If, on the other hand, the user rejects the insulin recommendation, hardware and/or software forming part of the system 10 allows the user to override the system 10 and manually enter insulin bolus quantity, type, and/or timing. The system 10 is then configured in a manner to automatically infuse or otherwise provide the user specified amount, type, and/or timing of insulin to the user's body in the form of one or more insulin boluses.

The appropriate amount and type of insulin corresponding to the insulin recommendation displayed by the system 10 may be manually injected into, or otherwise administered to, the user's body. It will be understood, however, that the system 10 may additionally be configured in like manner to determine, recommend, and/or deliver other types of medication to a user.

System 10 is operable to determine and either recommend or administer an appropriate amount of insulin or other glucose lowering drug to the user in the form of one or more insulin boluses. In determining such appropriate amounts of insulin, system 10 requires at least some information relating to one or more external influences and/or various physiological mechanisms associated with the user. For example, if the user is about to ingest, is ingesting, or has recently ingested, a meal or snack, the system 10 generally requires some information relating to the meal or snack to determine an appropriate amount, type and/or timing of one or more meal compensation boluses. When a person ingests food in the form of a meal or snack, the person's body reacts by absorbing glucose from the meal or snack over time. For purposes of this disclosure, any ingesting of food may be referred to hereinafter as a "meal," and the term "meal" therefore encompasses traditional meals, for example, breakfast, lunch and dinner, as well as intermediate snacks, drinks, etc.

Referring to FIG. 2, in some embodiments, in order for continuous glucose monitoring and/or control system 10, including controller 12, pump 35, and sensor 31, to be most effective in treating a user 63, a user information profile 64 and optimal control parameters 65 are provided. In one embodiment, certain control parameters, for example, target glucose threshold, an overall glucose safe range, and the like can often be predetermined based on known values for common user types and are typically known in the art. Other embodiments may supplement known ranges by information observed and determined by user's 63 health care provider ("HCP"). In some embodiments, user information profile 64 includes information specific to patient 63, including a quantified glucose absorption profile created based on, for example, body type, race, known tolerances, historical data and the like.

The general shape of a glucose absorption profile for any person rises following ingestion of the meal, peaks at some measurable time following the meal, and then decreases thereafter. The speed, that is, the rate from beginning to completion, of any one glucose absorption profile typically varies for a person by meal composition, by meal type or time (for example, breakfast, lunch, dinner, or snack) and/or according to one or more other factors, and may also vary from day-to-day under otherwise identical meal circumstances. Generally, the information relating to such meal intake information supplied by the user to the system 10 should contain, either explicitly or implicitly, an estimate of the carbohydrate content of the meal or snack, corresponding to the amount of carbohydrates that the user is about to ingest, is ingesting, or has recently ingested, as well as an estimate of the speed of overall glucose absorption from the meal by the user.

The estimate of the amount of carbohydrates that the user is about to ingest, is ingesting, or has recently ingested, may be provided by the user in any of various forms. Examples include, but are not limited to, a direct estimate of carbohydrate weight (for example, in units of grams or other convenient weight measure), an amount of carbohydrates relative to a reference amount (for example, dimensionless), an estimate of meal or snack size (for example, dimensionless), and an estimate of meal or snack size relative to a reference meal or snack size (for example, dimensionless). Other forms of providing for user input of carbohydrate content of a meal or snack will occur to those skilled in the art, and any such other forms are contemplated by this disclosure.

The estimate of the speed of overall glucose absorption from the meal by the user may likewise be provided by the user in any of various forms. For example, for a specified value of the expected speed of overall glucose absorption, the glucose absorption profile captures the speed of the meal taken by the user. As another example, the speed of overall glucose absorption from the meal by the user also includes time duration between ingesting of the meal by a person and the peak glucose absorption of the meal by that person, which captures the duration of the meal taken by the user. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (for example, units of time), a compound parameter corresponding to meal speed or duration relative to a reference meal speed or duration (for example, dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount and carbohydrate amount (for example, in units of grams) in conjunction with a carbohydrate content estimate in the form of meal size or relative meal size, an estimate of fat amount, protein amount and carbohydrate amount relative to reference fat, protein and carbohydrate amounts in conjunction with a carbohydrate content estimate in the form of meal size or relative meal size, and an estimate of a total glycemic index of the meal or snack (for example, dimensionless). The term "total glycemic index" is defined for purposes of this disclosure as a parameter that ranks meals and snacks by the speed at which the meals or snacks cause the person's blood sugar to rise. Thus, for example, a meal or snack having a low glycemic index produces a gradual rise in blood sugar whereas a meal or snack having a high glycemic index produces a fast rise in blood sugar. One exemplary measure of total glycemic index may be, but is not limited to, the ratio of carbohydrates absorbed from the meal and a reference value, for example, derived from pure sugar or white bread, over a specified time period, for example, 2 hours. Other forms of providing for user input of the expected overall speed of glucose absorption from the meal by the user, and/or for providing for user input of the expected shape and duration of the glucose absorption profile generally will occur to those skilled in the art, and any such other forms are contemplated by this disclosure.

Generally, the concentration of glucose in a person with diabetes changes as a result of one or more external influences such as meals and/or exercise, and may also change resulting from various physiological mechanisms such as stress, menstrual cycle and/or illness. In any of the above examples, the system 10 responds to the measured glucose by determining the appropriate amount of insulin to administer in order to maintain normal glucose levels without causing hypoglycemia. In some embodiments, the system 10 is implemented as a discrete system with an appropriate sampling rate, which may be periodic, aperiodic or triggered, although other continuous systems or hybrid systems may be implemented as described above.

As one example of a diabetes control system, one or more software algorithms may include a collection of rule sets which use (1) glucose information, (2) insulin delivery information, and/or (3) subject inputs such as meal intake, exercise, stress, illness and/or other physiological properties to provide therapy, etc., to manage the user's glucose level. The rule sets are generally based on observations and clinical practices as well as mathematical models derived through or based on analysis of physiological mechanisms obtained from clinical studies. In the exemplary system, models of insulin pharmacokinetics and pharmacodynamics, glucose pharmacodynamics, meal absorption and exercise responses of individual users are used to determine the timing and the amount of insulin to be delivered. A learning module may be provided to allow adjustment of the model parameters when the user's overall performance metric degrades (for example, adaptive algorithms, using Bayesian estimates, may be implemented). An analysis model may also be incorporated which oversees the learning to accept or reject learning. Adjustments are achieved utilizing heuristics, rules, formulae, minimization of cost function(s) or tables (for example, gain scheduling).

Predictive models can be programmed into the processors of the system using appropriate embedded or inputted software to predict the outcome of adding a controlled amount of insulin or other drug to a user in terms of the an expected glucose value. The structures and parameters of the models define the anticipated behavior.

Any of a variety of controller design methodologies, such as PID systems, full state feedback systems with state estimators, output feedback systems, LQG controllers, LQR controllers, eigenvalue/eigenstructure controller systems, and the like, could be used to design algorithms to perform physiological control. They typically function by using information derived from physiological measurements and/or user inputs to determine the appropriate control action to use. While the simpler forms of such controllers use fixed parameters (and therefore rules) for computing the magnitude of control action, the parameters in more sophisticated forms of such controllers may use one or more dynamic parameters. In some embodiments, the one or more dynamic parameters take the form of one or more continuously or discretely adjustable gain values. In some embodiments, specific rules for adjusting such gains are defined on an individual basis, and, in other embodiments, on the basis of a user population. In either case these rules will typically be derived according to one or more mathematical models. Such gains are scheduled according to one or more rule sets designed to cover the expected operating ranges in which operation is typically nonlinear and variable, thereby reducing sources of error.

Model based control systems, such as those utilizing model predictive control algorithms, can be constructed as a black box wherein equations and parameters have no strict analogs in physiology. Rather, such models may instead be representations that are adequate for the purpose of physiological control. The parameters are typically determined from measurements of physiological parameters such as glucose, insulin concentration, and the like, and from physiological inputs such as food intake, alcohol intake, insulin doses, and the like, and also from physiological states such as stress level, exercise intensity and duration, menstrual cycle phase, and the like. These models are used to estimate current glucose or to predict future glucose values. Such models may also take into account unused insulin remaining in the blood after a bolus is given, for example, in anticipation of a meal. Such unused insulin will be variously described as unused, remaining, or "insulin on board."

Insulin therapy is derived by the system based on the model's ability to predict glucose for various inputs. Other modeling techniques may be additionally used including for example, but not limited to, building models from first principles.

As described above, system 10 includes an analyte monitor that continuously monitors the glucose levels in a user. The controller module is programmed with appropriate software and uses models as described above to predict the effect of carbohydrate ingestion and exercise, among other factors on the predicted level of glucose. Such a model must also take into account the amount of insulin remaining in the blood stream from a previous bolus or basal rate infusion when determining what or whether or not to provide a bolus of insulin.

The controller module is typically programmed to provide a "basal rate," which is the rate of continuous supply of insulin by an insulin delivery device such as a pump that is used to maintain a desired glucose level in the bloodstream of a user. Periodically, due to various events that affect the metabolism of a user, such as eating a meal or engaging in exercise, a "bolus" is required. A "bolus" is a specific amount of insulin that is required to raise the blood concentration of insulin to an effective level to counteract the effects of the ingestion of carbohydrates during a meal and also takes into account the effect of exercise on the glucose level.

In some embodiments, system 10 includes a number of medical devices 30, 32, including, but not limited to, a CGM sensor 31 and insulin pump 35. As such, electronic device 12 or medical device 30, 32, in an integrated system, may represent a device which performs the intended function of several of these components. One purpose of the safety layer is to envelop critical components of diabetes control system 10 (depicted by FIGS. 2 and 3) with a safety layer that maximizes the modularity of system components with respect to value constraints that can change due to component hardware and software upgrades over the life of system 10.

FIG. 2 shows a typical closed loop system using sensor 31 as a means to monitor glucose level in a user and insulin pump 35 as a means to regulate glucose. As long as the hard limits (for example, a maximum delivery rate) and other limits due to safety considerations are accounted for, then the system should operate as intended, thus keeping glucose levels healthy and preventing diabetes-related complications. The dashed outline 66 represents the boundary of components provided by the system. As depicted by the drawings of the embodiments, the safety layer maintains these boundary input/output conditions so that outside designers can then use rapid controller development environments to perform artificial pancreas research and development, as well as design and/or development of new control algorithms and/or new controllers. For example, software could be ported into a future controller module product with minimal code change to software within other components of the overall system.

In some embodiments, controller module 12 includes a bridge between CGM sensor 31 and pump 35, but may not be designed by the same pump or sensor designer/manufacturer. Further, the controller module may include a software algorithm that is updated over time to accommodate change in necessary calculations based on a user's status, or change in technology. The pump and/or sensor may also require updated hardware or software, or may be changed due to further changes in technology or unforeseen problems with past design. The dissimilarity between pump and sensor and controller may cause potential conflicts due to unforeseen incompatibilities between the system components. Thus, the safety layer is directed to a wrapper around pump 35 and sensor 31 with the anticipation that the controller module may be designed by an outside/third-party designer/manufacturer. In other embodiments, the safety layer is equally applicable to controller modules. The features of the safety layer and its components and hardware and/or software may be incorporated into controller module hardware and/or software using the same techniques.

The safety layer in accordance with aspects of the present invention is implemented by incorporating a model that takes into account the characteristics of pump 21 and CGM sensor 31 within system 10. Since one company's design may determine the evolution of the hardware and software components of pump 35 and CGM sensor 31, safety layer 100 preferably resides around these components.

In one embodiment, still referring to FIG. 2, the interface boundaries 66 of safety layer (shown by a dotted line) manages signals between pump 35 and/or CGM sensor 31 and control module 12. When an algorithm is designed for a system with a specific pump, and the pump is replaced by another one whose maximum basal rate is significantly lower than the previous pump, or one whose maximum bolus amount is significantly lower than the previous pump, the absence of the safety layer requires a redesign of the control algorithm. Failure to do so could result in the mismatch between predicted glucose and observed glucose (through one or more glucose measuring devices) to be perceived as a model parameter mismatch and/or internal state discrepancy to be compensated further. Depending on the dynamic interaction between the assumed model and the controller structure, this further compensation, which will not likely assume an input limitation mismatch, could result in unnecessarily large or small insulin amount to be delivered in the subsequent sample instances. At best, this could cause a drift in how the actual glucose tracks a desired profile. One undesirable scenario is a windup phenomenon which results in an exaggerated overshoot towards hyperglycemia, followed by hypoglycemia. To solve these problems, in one aspect, interface 66 manages safety constraints and hardware and/or software limits that may not be taken into account explicitly by a particular control algorithm architecture or hardware. It also allows outside development of many independent control algorithms and/or hardware devices while at the same time ensuring that safety limits are accounted for, and further allows minimal control algorithm change when a component with specific hard limits is replaced-by another component with different hard limits.

Figure 3:
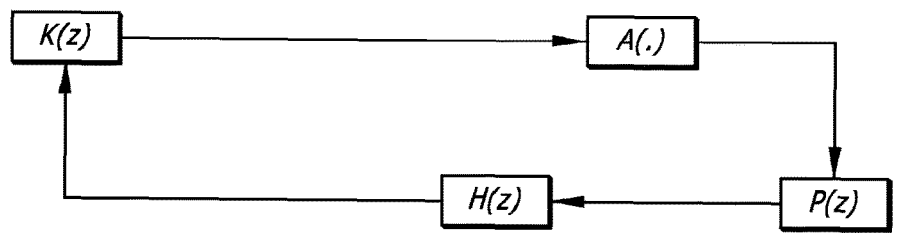
FIG. 3 depicts an IDM system of FIG. 2 further illustrated by transfer functions.

The depicted closed loop system can be modeled by transfer functions $A(.)$, $P(z)$, and $H(z)$. FIG. 3 illustrates a closed loop system that includes of: (1) a pump as an actuator $A(.)$ whose output is bounded by constants on the upper and lower limits, (2) a user represented by a dynamic user model $P(z)$, (3) a sensor model $H(z)$, and (4) controller model $K(z)$ designed to determine the proper actuator output at specific time intervals based on information partially provided by the sensor unit. Any model whose transfer function is described using the z operator implies that a linear version is possible, such that a linear transfer function can be created using z transform to represent a model. These models are embodied by their respective modules (for example, controller module) which may be further incorporated in, or represented by, sensor 31, pump 35, and electronic device 12. Actuator module $A(.)$ is the only module that has a more generic notation "$(.)$" because the output bounds do not allow for a linear model representation.

Figure 4A:
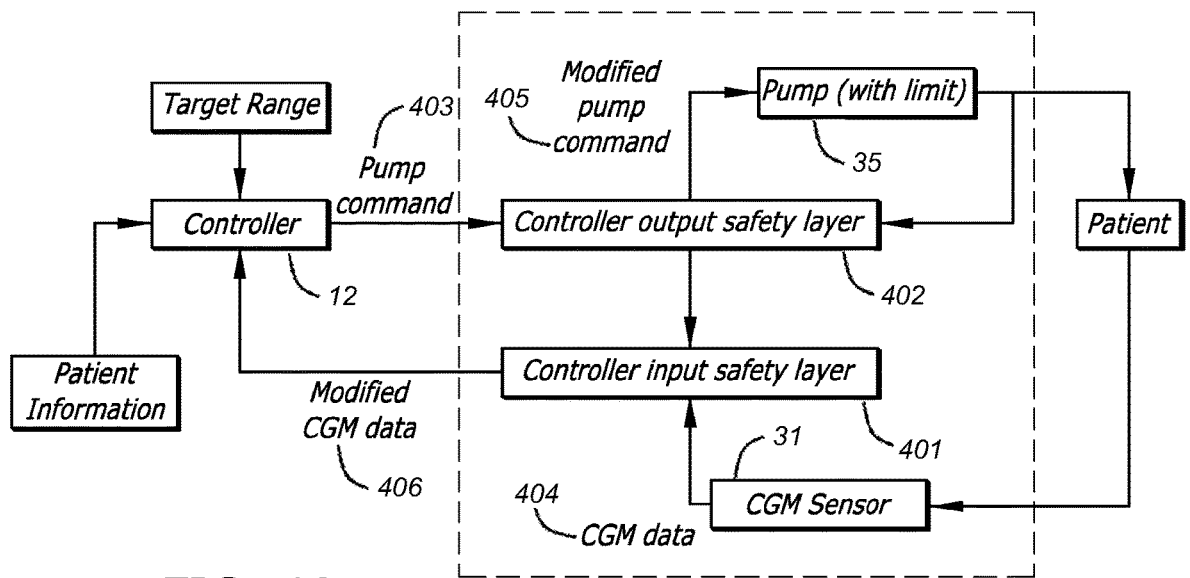
FIG. 4A depicts an embodiment of a safety layer as two distinct components.
Figure 4B:
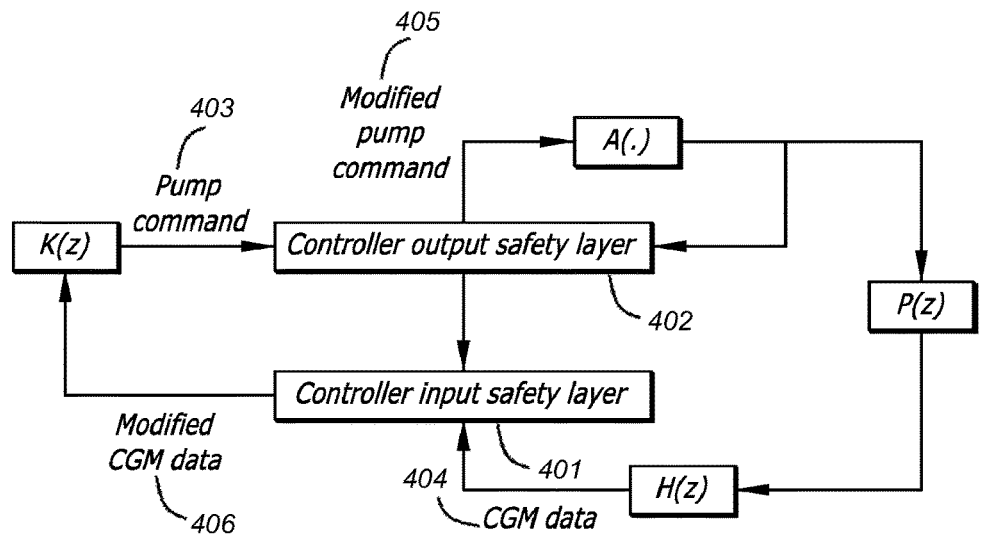
FIG. 4B depicts a diagram of the feedback portion of an IDM system, including the safety layer, in accordance with aspects of the present invention.

Turning to FIGS. 4A and 4B, the present embodiment uses a control design architecture as a safety layer to compensate for, and manage, systems with bounded input, state, and/or output. Safety layer may include one or more hardware and/or software components and/or modules, and, thus, for the purpose of this disclosure, the safety layer may be referred to as multiple modules or as a single module interchangeably. In the depicted embodiment, the safety layer includes multiple components/modules. A controller input safety layer 401 and a controller output safety layer 402 are depicted as integrated in IDM system 10. Input safety layer 401 modifies the CGM sensor signal to the controller module and output safety layer 402 modifies the controller module's action (for example, for an insulin bolus amount) to the actuator (for example, an insulin pump). The modifications are made such that the stability of the system under these known bounds is preserved and that there is minimal performance degradation should a particular controller module (which may be developed by an outside designer) fail to account for one or more bounds/limits. The main benefit is that modularity of the components, such as an outside-designed control algorithm or a presently designed pump, etc., is maximized while minimizing the hazard of exceeding certain limits imposed by these components.

In some embodiments, control module 12 is primarily responsible for comprising the control algorithm. In one embodiment, the safety layer may not need to be aware of the particular control algorithm architecture, although it knows the value of the latest control actions. Such control actions include, but are not exclusive to insulin and/or glucagon delivery. In this embodiment, the safety layer merely serves as an outer layer to a particular control algorithm architecture designed by any outside designer.

For example, consider the case of an insulin pump 35 that replaces one with a different maximum delivery rate. To a certain extent, the safety layer can make necessary adjustments without requiring any adjustment to the control algorithm designed by an outside designer. When the control algorithm issues a delivery rate that is higher than the current pump's ability, the safety layer keeps track of the necessary correction that needs to be made in the subsequent sample times in order to prevent system instability or limit cycles from occurring.

All correction tracking data, state, values of past and present control actions and other data and information are converted to digital data and stored in a memory module for retrieval by the safety layer system. In one embodiment, the memory module is a hardware component that is part of a separate safety layer hardware circuitry. In another embodiment, the safety layer is configured to use existing memory of either the pump or CGM sensor systems.

In order to ensure that the known limits are accounted for without depending on the particular combination of controller architecture and/or hardware components such as the particular pump model, a safety layer can be constructed as shown in FIG. 4A. In this embodiment, when controller 12 does not account for a limit set by the pump architecture, the safety layer will intervene appropriately by making adjustments to the pump command 403 and CGM data 404, transforming them into a modified pump command 405 and modified CGM data 406, respectively. Otherwise, the safety layer will remain idle in the background providing no change to the signal.

In a further embodiment, still referring to FIGS. 4A and 4B, the safety layer exists as two distinct components. As shown by FIG. 4B, without loss of generality, a feed forward component of the outside designer's controller is ignored, and the system looks only at the effect of the feedback component expressed as a discrete time transfer function, K(z). In this embodiment, pump 35 is expressed as a nonlinear model A(.) due to the insulin delivery limit, the user is expressed in terms of P(z), and CGM sensor 31 is expressed in terms of H(z).

Figure 5:
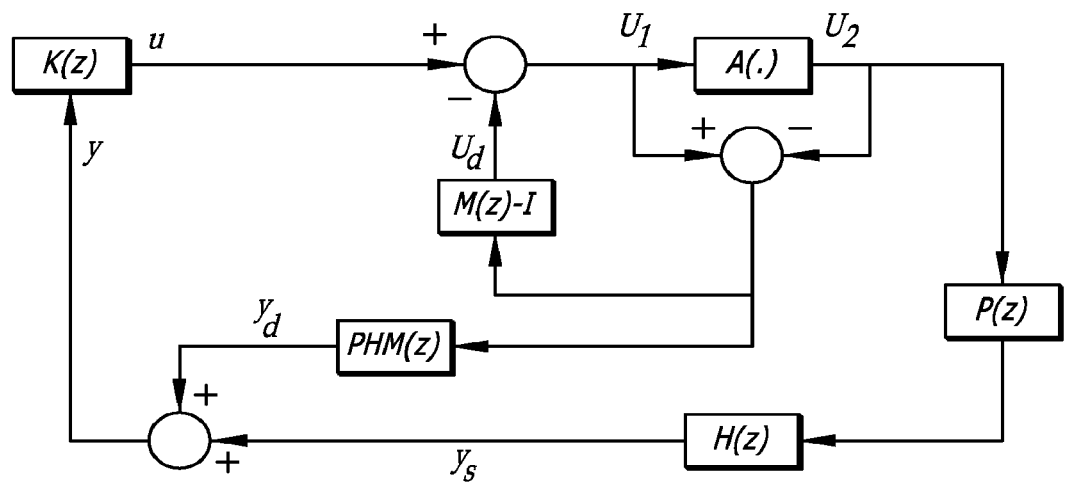
FIG. 5 depicts a diagram of the IDM system using a safety layer comprising linear conditioning.

In one embodiment, shown by FIG. 5, a controller architecture called Linear Conditioning is used as a safety layer. The safety layer is now represented by specific transfer functions. To this end, the top part contains two modules that can be designed, namely M(z)−I and PHM(z), in which the P(z) and H(z) are determined a priori by the model of the "user" and "sensor," respectively.

The role of M(z)−I is to minimize the decay time of the unwanted effect of a saturation event into the system.

The role of PHM(z) is to minimize the peak transient amplitude of the unwanted effect of a saturation event into the system at any given time.

The term "saturation event" in this context implies an event in which the controller module K(z) generates a command that exceeds the actuator bounds. Since M(z) is the only tunable model, this becomes a tradeoff between tuning M(z) to minimize decay time or to minimize any transient peaks. For example, designing M(z) to minimize decay time only may result in PHM(z) allowing one or more large transient peaks to propagate into the system output (and system behavior). On the other hand, designing M(z) to minimize transient peaks may result in the transients due to a saturation event to last a very long time. The second consideration in addition to the tradeoff is that M(z) must be tuned such that the feedback path in FIG. 4 comprising the I-A(.) block and the M(z)-I block is stable, and that the PHM(z) block is Bounded-Input-Bounded-Output (BIBO) stable. It should be noted that a system/block is BIBO stable if given a bounded input, the output remains bounded as well. Moreover, the details of tuning M(z) to meet the described set of criteria is a process common to those skilled in the art of control system design.

A modified pump command is thus represented by $$u_1(z) = u(z) - u_d(z)$$

wherein $$u_d(z) = [M(z) - I][I - A(.)]u_1(z)$$

In these equations I represents the identity function, and M(z) is the only design element when the Linear Conditioning architecture is used.

The first line converts the pump command u(z) into modified pump command $u_1(z)$. The second line keeps track of the modified pump command to be delivered in future sample times based on all prior modified pump commands. This is the component that ensures that any inaccuracies caused by reduced pump output are accounted for in the future. The only component that is not directly based on any of the system assumption is the transfer function M(z).

The second group, the controller input safety layer, consists of the following set of equations:

$$y(z) = y_s(z) + y_d(z)$$

$$y_d(z) = PHM(z)[I - A(.)]u_1(z)$$

The first line converts the CGM output $y_s(z)$ into a modified output y(z) as seen by the feedback controller K(z).

Figure 6:
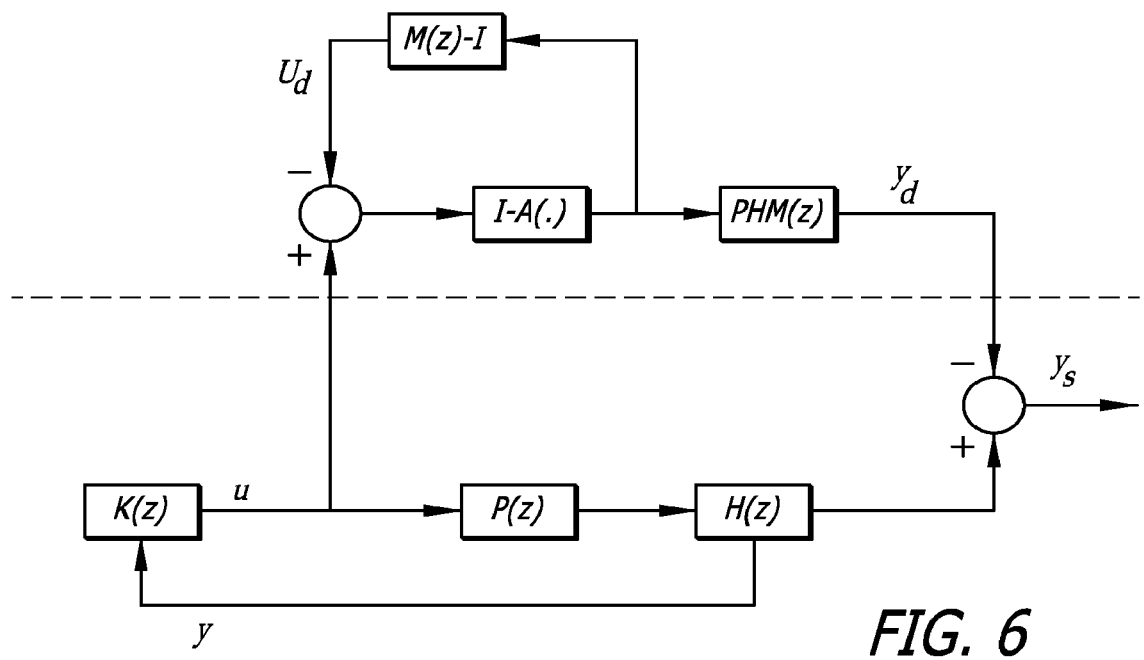
FIG. 6 depicts an equivalent diagram of the IDM system using a safety layer comprising linear conditioning.

The second line keeps track of how the output should be modified based on all prior modified pump commands. The term PHM(z) corresponds to the time convolution of the user model P(z), CGM model H(z), and M(z) previously described FIG. 5 is illustrative of one example of linear conditioning as a safety layer. The role of the linear conditioning modules as a safety layer can be best explained by rearranging the diagram in FIG. 5 into FIG. 6. The equivalent block shown in FIG. 6 illustrates that when designed properly, the system could be viewed as two different parts. The first (or lower) part includes the controller module K(z), user module P(z), and sensor module H(z). As long as the controller does not generate signals that saturate the actuator, then the modules in the second (or upper) part will not generate any signal that affects the system, and the overall system behavior will be in accordance with the system without saturation limits. However, if K(z) generates a signal that exceeds the actuator's bounds, blocks in the upper area will exhibit a transient. When this occurs, the modules M(z)−I and PHM(z) attempts to minimize the peak and duration of the transient disturbance caused by the saturation. These modules are designed with parameters to preserve stability of the overall system.

The components above the dashed line remain inactive until the controller K(z) issues a command that exceeds a certain limit. Hence, as long as the limit is not exceeded, the system behaves as if the limit does not exist, as indicated by the fact that the elements below the dashed line are only the nominal components of the system minus the limit and the Linear Conditioning modules.

An exemplary system incorporates physiological models of insulin and glucose compartments. The intent is not to choose a specific model, rather to illustrate how the safety mechanism described herein can be practiced.

Suppose the user's insulin response to a sub-cutaneous insulin infusion (from the actuator) can be described by the following continuous time domain set of equations:

$$\dot{S} = -k_a S + u_I$$

$$\dot{I} = -k_e I + \left(\frac{k_a}{V_I}\right) S$$

$$\dot{x}_E = k_{aE}(-x_E + I)$$

$$\dot{x}_T = k_{aT}(-x_T + I)$$

$$\dot{x}_D = k_{aD}(-x_D + I)$$

Where $u_I$ is the subcutaneously delivered insulin infusion rate from the actuator, S is an intermediary plasma insulin compartment, I is the plasma insulin concentration, and $x_E$, $x_T$, and $x_D$ correspond to the effective insulin compartments that affect endogenous glucose production, glucose transport, and glucose disposal, respectively. $V_I$ corresponds to total insulin volume, and parameters k* correspond to decay rates of each corresponding compartment.

Suppose the user's glucose response to effective insulin can be described by the following 3 compartment model:

$$\dot{g}_b = -x_T g_b + k_{b/h} g_h + f(x_E)$$

$$\dot{g}_h = -x_D g_h + x_T g_b$$

$$\dot{g}_i = k_{ai}(-g_i + g_b)$$

Where $g_b$, $g_h$, and $g_i$ are glucose in the blood, hepatic, and interstitial compartments.

Suppose the sensor can be modeled by the following equation:

$$y = \frac{1}{V_G} g_i$$

Where $V_G$ is the glucose volume, such that the sensor reads glucose concentration instead of glucose amount. Note that without loss of generality, the non-trivial task of calibrating the sensor such that it generates signals that are appropriately calibrated into glucose concentration units is assumed to be provided by one or more modules outside the scope of this discussion. As a result, the measurement y is specified in terms of the appropriate unit. In at least one embodiment sensor noise is assumed to be negligible.

The equations described thus far make up the equations used to represent the user P and sensor H models. Putting the equations together, and linearizing the equations at every operating point, one obtains the following state space equation in the continuous time domain:

$$\frac{d}{dt}\begin{bmatrix} S \\ I \\ x_E \\ x_T \\ x_D \\ g_b \\ g_h \\ g_i \end{bmatrix} = \begin{bmatrix} -k_a & 0 & 0 & 0 & 0 & 0 & 0 & 0 \\ k_a/V_I & -k_e & 0 & 0 & 0 & 0 & 0 & 0 \\ 0 & k_{aE} & -k_{aE} & 0 & 0 & 0 & 0 & 0 \\ 0 & k_{aT} & 0 & -k_{aT} & 0 & 0 & 0 & 0 \\ 0 & k_{aD} & 0 & 0 & -k_{aD} & 0 & 0 & 0 \\ 0 & 0 & \frac{f(x_E)}{x_E}\bigg|_{t=k} & 0 & 0 & -x_T|_{t=k} & \frac{k_b}{h} & 0 \\ 0 & 0 & 0 & 0 & 0 & x_T|_{t=k} & x_D|_{t=k} & 0 \\ 0 & 0 & 0 & 0 & 0 & k_{ai} & 0 & k_{ai} \end{bmatrix} \begin{bmatrix} S \\ I \\ x_E \\ x_T \\ x_D \\ g_b \\ g_h \\ g_i \end{bmatrix} + \begin{bmatrix} 1 \\ 0 \\ 0 \\ 0 \\ 0 \\ 0 \\ 0 \\ 0 \end{bmatrix} u_I$$

$$y = \begin{bmatrix} 0 & 0 & 0 & 0 & 0 & 0 & 0 & \frac{1}{V_G} \end{bmatrix} \begin{bmatrix} S \\ I \\ x_E \\ x_T \\ x_D \\ g_b \\ g_h \\ g_i \end{bmatrix} + [0] u_I$$

Define the following:

$$x_{PH} := \begin{bmatrix} S \\ I \\ x_E \\ x_T \\ x_D \\ g_b \\ g_h \\ g_i \end{bmatrix},$$

$$A := \begin{bmatrix} -k_a & 0 & 0 & 0 & 0 & 0 & 0 & 0 \\ k_a/V_I & -k_e & 0 & 0 & 0 & 0 & 0 & 0 \\ 0 & k_{aE} & -k_{aE} & 0 & 0 & 0 & 0 & 0 \\ 0 & k_{aT} & 0 & -k_{aT} & 0 & 0 & 0 & 0 \\ 0 & k_{aD} & 0 & 0 & -k_{aD} & 0 & 0 & 0 \\ 0 & 0 & \frac{f(x_E)}{x_E}\bigg|_{t=k} & 0 & 0 & -x_T|_{t=k} & \frac{k_b}{h} & 0 \\ 0 & 0 & 0 & 0 & 0 & x_T|_{t=k} & x_D|_{t=k} & 0 \\ 0 & 0 & 0 & 0 & 0 & k_{ai} & 0 & k_{ai} \end{bmatrix}$$

$$B := \begin{bmatrix} 1 \\ 0 \\ 0 \\ 0 \\ 0 \\ 0 \\ 0 \\ 0 \end{bmatrix}, C := \begin{bmatrix} 0 & 0 & 0 & 0 & 0 & 0 & 0 & \frac{1}{V_G} \end{bmatrix}, D := [0], u := u_I$$

Then, the user-sensor model PH can be described using the state space representation (A, B, C, D), where:

$$\dot{x}_{PH} = A x_{PH} + Bu$$

$$y = C x_{PH} + Du$$

Laplace transform can be applied to the continuous time domain state space description above to obtain PH(s), and any suitable discretization method such as zero-order-hold can be used to create the z-transform equivalent PH(z) referenced in FIGS. 2, 3B, 4, and 5. It should be noted that the particular choice of the model used in the above illustration does not constrain this implementation. Rather, it provides a more concrete example in the derivation of the state space representation (A, B, C, D) of the user-sensor module combination PH, and that methods to describe this combination in the z domain PH(z) exist and will not be discussed in further detail.

While there are many different ways to design the Linear Conditioning modules M(z)−I and PHM(z), one method called Direct M Design, as used in Weston and Postlethwaite, *Linear Conditioning for Systems Containing Saturating Actuators, Automatica*, 36:1347-1354, 2000, incorporated herein by reference, is described here due to the benefit of being able to directly derive most of the linear conditioning (LC) structure and parameters from the user and sensor model assumption. The design is performed in the continuous time domain first, and converted to discrete time at the end. The continuous time domain state space representation of M depends explicitly on the user and sensor model plus a design parameter F. In particular, M is expressed as ([A+BF], B, F, I), where I is an identity matrix.

F is chosen such that [A+BF] is stable. One example is to use pole placement method such that the Eigen values remain on the left half plane of the s-domain. In addition, F is tuned to obtain a reasonable tradeoff between the peak disturbance caused by saturation and the time it takes to completely attenuate the disturbance due to saturation. The faster the Eigen values of [A+BF] are, the less time it takes to completely attenuate a disturbance due to saturation.

The design of safety layer 100 does not require knowledge of the controller module K(z). Rather, the design (in this case the tuning of the matrix F) depends solely on the user model, and to some degree, the sensor model. Pole placement and other stabilizing feedback design techniques can be used to determine the best F when new actuator saturation limits are enforced by a component change or other considerations. Once the values of the matrix F have been determined, the first module of the LC, M(z)-I, can be obtained by first arranging the continuous time domain version described in state space as:

$$\dot{x}_{LC} = \left(\begin{bmatrix} -k_a & 0 & 0 & 0 & 0 & 0 & 0 & 0 \\ k_a/V_I & -k_e & 0 & 0 & 0 & 0 & 0 & 0 \\ 0 & k_{aE} & -k_{aE} & 0 & 0 & 0 & 0 & 0 \\ 0 & k_{aT} & 0 & -k_{aT} & 0 & 0 & 0 & 0 \\ 0 & k_{aD} & 0 & 0 & -k_{aD} & 0 & 0 & 0 \\ 0 & 0 & \frac{f(x_E)}{x_E}\Big|_{t=k} & 0 & 0 & -x_T|_{t=k} & \frac{k_b}{h} & 0 \\ 0 & 0 & 0 & 0 & 0 & x_T|_{t=k} & x_D|_{t=k} & 0 \\ 0 & 0 & 0 & 0 & 0 & k_{ai} & 0 & k_{ai} \end{bmatrix} + \begin{bmatrix} 1 \\ 0 \\ 0 \\ 0 \\ 0 \\ 0 \\ 0 \\ 0 \end{bmatrix} F \right) x_{LC} + \begin{bmatrix} 1 \\ 0 \\ 0 \\ 0 \\ 0 \\ 0 \\ 0 \\ 0 \\ 0 \end{bmatrix} u_s$$

$$u_d = F x_{LC} + [0] u_s$$

Where $u_d$ is the continuous time domain output of the first module, and $u_s$ is the difference between $u_1$ and $u_2$ as shown in FIG. 5, and $x_{LC}$ is the set of internal states of the LC. It has no direct physical meaning and can be expressed in infinitely many other realizations. Practically, a particular realization is chosen from a numerical condition perspective. One method to achieve this is to transform the realization into one that is called a balanced realization. The state space above can be expressed in a more compact form as:

$$\dot{x}_{LC} = [A+BF]x_{LC} + Bu_s$$

$$u_d = F x_{LC}$$

The z transform from $u_s$ to $u_d$ obtained by discretizing the continuous time domain state space equation ([A+BF], B, F, 0) above is the M(z)−I module described in FIG. 5.

The second LC component is the PHM(z) module, where, given the above construct, is first described in terms of continuous time domain state space equation shown below:

$$\dot{x}_{LC} = [A+BF]x_{LC} + Bu_s$$

$$y_d = [C+DF]x_{LC} + Du_s$$

Again, the z transform from $u_s$ to $y_d$ can be obtained by discretizing the continuous time domain state space equation ([A+BF], B, [C+DF], D) above to get PHM(z).

Note that the continuous time domain state space equations used to derived both M(z)−I and PHM(z) share the same dynamic element. This owes to the fact that the dynamic element is driven by the user-sensor model (A, B, C, D) and the tunable LC matrix F. Equivalently, one can define a continuous time domain state space representation as follows:

$$\dot{x}_{LC} = [A+BF]x_{LC} + Bu_s$$

$$\begin{bmatrix} u_d \\ y_d \end{bmatrix} = \begin{bmatrix} F \\ C+DF \end{bmatrix} x_{LC} + \begin{bmatrix} 0 \\ D \end{bmatrix} u_s$$

And then obtain the z transform equivalent to compute the outputs $u_d$ and $y_d$ of the M(z)−I and PHM(z) modules in response to the difference between the unsaturated and saturated control commands $u_1$ and $u_2$.

FIG. 6 is illustrative of an equivalent representation of the feedback system using Linear Conditioning as a safety layer. Once a limit is exceeded, the command u issued by the controller K(z) that enters a feedback path above the dashed line can no longer be blocked by the element I−A(.), which is the complement of the saturation function. This starts an initial condition to the upper feedback path, eventually "contaminating" the actual output of the sensor, $y_s$. This is where the design of M(z) is made such that the transient due to the command u exceeding a limit is as minimal as possible.

The safety layer is transparent to outside designers, such that it will only intervene when a particular value constraint is not met by a particular controller. If, for instance, electronic device 12 issues a command to pump 35 within the limits of the pump, and the pump is readily able to process, the safety layer will not activate and the command will be directly routed to the pump. If, on the other hand, the command issued includes a value outside the pump's maximum delivery rate the safety layer will intervene and the output signal will be modified and input and output and safety parameters stored, for instance, in memory 40 (of pump 35). The safety layer will then proceed to manage output commands based on the stored data, including modified pump commands to be delivered in future sample times based on all prior modified pump commands.

Figure 7B:
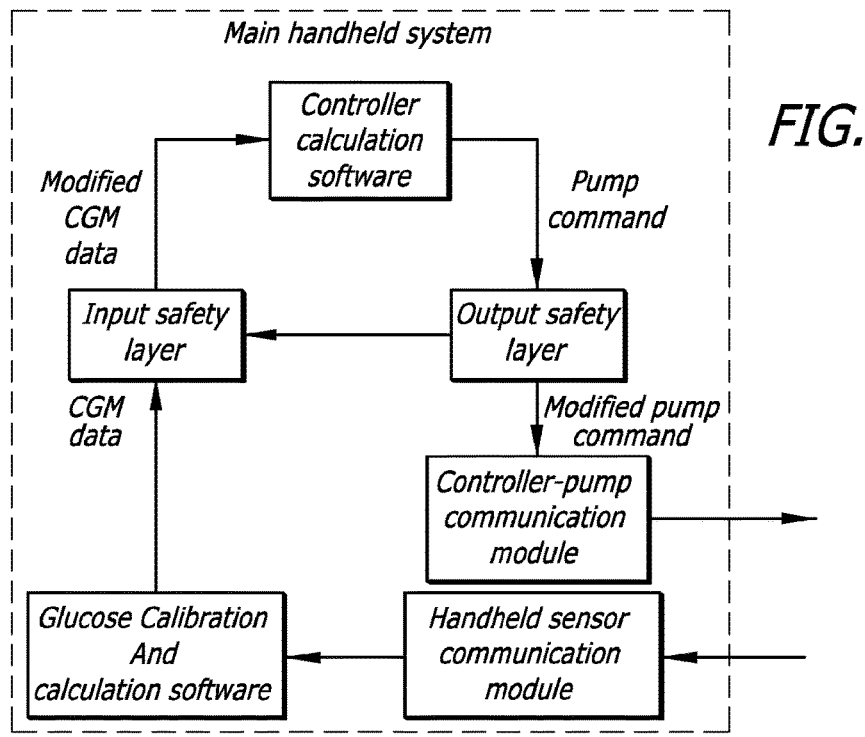
Figure 7C:
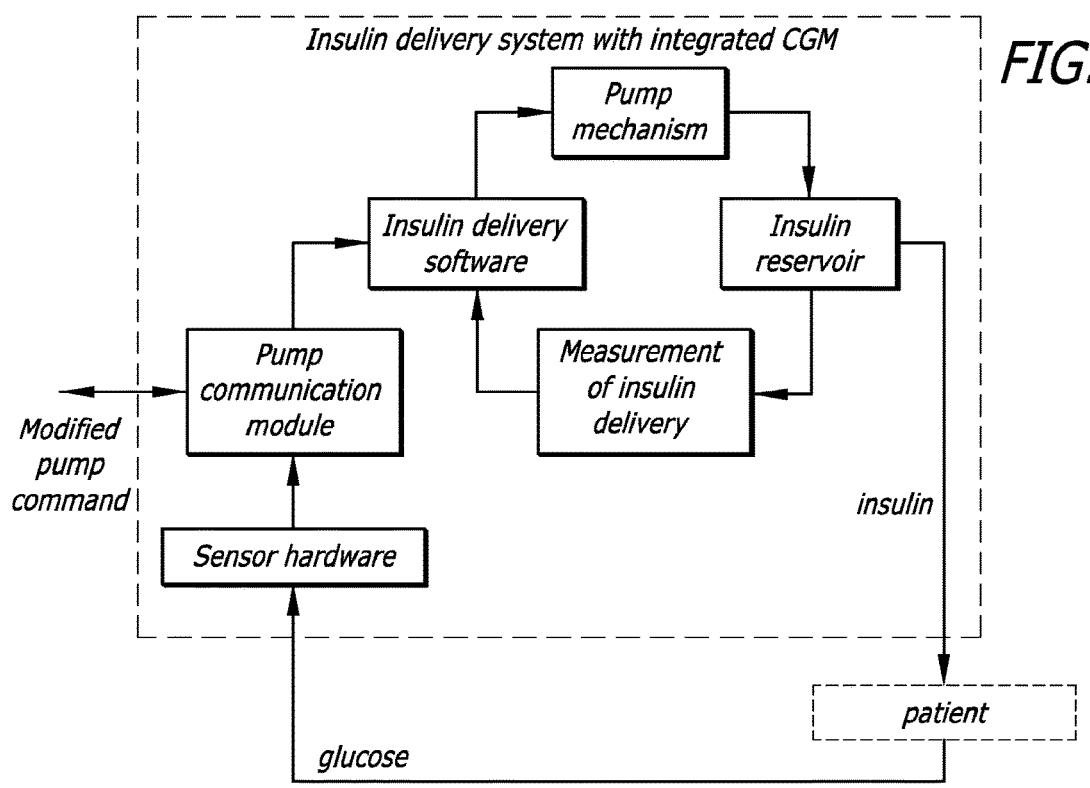
FIG. 7C shows an insulin delivery system having an integrated glucose monitor (CGM).

The safety layer may include one or more components each of which may further comprise either hardware or software modules, or a combination of both. Turning to FIG. 7A, system 10 is depicted to include a main controller system 701, insulin delivery system 702, CGM component 703, and handheld CGM component 704, that are collectively usable on a user 705. In some embodiments, electronic device 12 is part of, or includes main controller system 701. In some embodiments, main controller system 701 is part of, or includes, electronic device 12. In some embodiments, pump 35 is part of, or includes insulin delivery system 702. In some embodiments, insulin delivery system 702 is part of, or includes, pump 35. In some embodiments, sensor 31 is part of, or includes CGM component 703. In some embodiments, CGM component 703 is part of, or includes, sensor 31. In some embodiments, depicted by FIG. 7B, handheld CGM component 704 is part of, or integrated with main controller system 701. In some embodiments, depicted by FIG. 7C, CGM component 703 is part of, or integrated with insulin delivery system 702. In some embodiments, main controller system 701 is a handheld device, for example, a handheld glucose monitoring device, PDA, smart phone, or the like. In further embodiments, main controller system 701 includes a computer, such as a personal computer, laptop, computer gaming system, smart television, or the like. It should be apparent to those of ordinary skill in the art that various adaptations and modifications of the components of system 10, and combinations thereof, may be accomplished without departing from the spirit and the scope of the invention.

Referring to FIG. 7A, controller input safety layer 401 and controller output safety layer 402 are depicted as integrated in controller system 701. As previously shown, the safety layer components may be integrated in any of the above components and in a number of ways. In the depicted embodiment, CGM data 706 is received by input safety layer 401 from CGM component 703 via (optional) controller-communication module 707. Input safety layer 401 is configured to receive CGM data 706 from CGM component 703 (for example, via controller-communication module 707), adjust the CGM data values according to the algorithms described herein, and forward a modified CGM data 708 to software component module 709. In one embodiment, CGM data 706 is stored to a database operably connected to safety layer 401. In another embodiment, CGM data 706 is passed directly to safety layer 401 via an application programming interface (API). In another embodiment, CGM data 706 is stored to a database operably connected to software component 709.

Software component module 709, including controller calculation software 710 receives modified CGM data 708 from input safety layer 401 and performs its typical calculation (ignorant of the modification to CGM data 706) for generating a command 711 for insulin delivery to be sent to insulin delivery system 702. In some embodiments, software component module 709 receives modified CGM data 708 from a database. In one embodiment, this database is the same database operably connected to safety layer 401. In another embodiment, this database is operably connected to software component module 709. In further embodiments, modified CGM data is received by software component module 709 via an API operably connected with module 709 or safety layer 401.

Output safety layer 402 is configured to intercept pump command 711 from software component module 709, adjust the command parameters according to the algorithms described herein, and forward a modified pump command 712 to insulin delivery system 702. In some embodiments, output safety layer 402 receives pump command 711 from a database. In one embodiment, this database is the same database operably connected to input safety layer 401. In another embodiment, this database is operably connected to software component module 709. In another embodiment, this database is operably connected to output safety layer 402. It should be understood that each component described herein can have its own unique database, or collectively share data from a database or databases operably connected to other components. In further embodiments, pump command 711 is received by output safety layer 402 via an API operably connected with output safety layer 402 or software component module 709. Similarly, modified pump command 712 can be passed by database or by API.

In some embodiments, where controller system 701 and insulin system 702 are independent and separate components, modified pump command 712 is forwarded via a pump communication module 713. In some embodiments, output safety layer 402 is further configured to provide feedback information 714 to input safety layer 401 in accordance with the above disclosure. In some embodiments, feedback information 714 is passed to input safety layer 401 by manipulation of data in a database operably connected to input safety layer 401, and, in some embodiments, feedback information 714 is passed via an API between input safety layer 401 and output safety layer 402. In some embodiments, feedback information 714 is passed by a hardware connection using a hardware standard (for example, voltage/current driven). It should also be understood from the above disclosure that CGM data 706, modified CGM data 708, pump command 711, modified pump command 712, and/or feedback information 714 can be passed in the form of a hardware standard without deviating from the intent of the present invention.

In some embodiments, safety layer 100 includes a common interface for providing an input to the safety layer and for managing communication between the controller output/inputs, the safety layer, and ultimately, the pump and CGM sensor component systems. In some embodiments, safety layer includes a hardware component in which both input and outputs remain fixed to a hardware standard (for example, voltage/current driven). In one embodiment the outer interface remains fixed over time while the internal interface may change with updated design of the corresponding pump or CGM sensor. In some embodiments the interface includes voltage and/or current driven inputs. Such inputs may be analogue or digital. In these embodiments, the safety layer may comprise an additional memory, processor, communication I/O, and the like, which may be integrated with electronic device 12, or medical device 30, 32, or, in some embodiments comprise a separate safety device to be used in connection with diabetes control system 10.

In another embodiment the safety layer includes an algorithm that is part of a software component of the system. In this embodiment the algorithm may be incorporated into or encapsulated by the interface, or the algorithm may comprise a separate software component aggregated by the interface to the outside designer. In one embodiment the interface is a binary standard, for example, a dynamic linked library (DLL). In this embodiment the interface represents to outside designers a predefined group of related exposed software functions that are linked to an internal software class engine. The interface does not necessarily represent all the functions that the inner software class engine supports. The class engine provides control of the hardware and provides the safety layer algorithm that processes commands from the control module in accordance with the safety models herein described. An outside designer may then continue to update a control algorithm and/or the class engine, as long as the internal commands comply with the binary standard. Thus, as long as the binary interface remains constant, the class engine and related algorithm may be updated periodically to accommodate change in pump hardware or technology standards. The software including the interface may be downloaded into, for example, memory 40 of pump 35 to be processed by processor 33.

In one embodiment, as shown by FIGS. 4A and 4B, a safety layer is especially useful when allowed to interact between the sensor and controller module. In this embodiment the above described transfer function PHM(z) represents a saturation flowing as an input into CGM data received from the sensor so as to create the equation $y=y_d+y_s$. In this manner, CGM sensor data may be modified and the controller feedback loop intercepted. This allows the controller module to adjust accordingly to modified CGM data and account for diminished or increased insulin delivery as a result of adjustment by the safety layer. In one embodiment, also shown by FIGS. 4A and 4B, the safety layer allows for the safe interaction of all of the components without explicitly requiring the controller module K to necessarily be aware of the saturation constraints while at the same time maximizing system safety and performance. This is achieved without having to modify the controller module K because the two main elements of the safety layer, namely a controller output safety layer, and a controller input safety layer, modifies necessary signals in real-time to achieve this objective.

At any time, the controller output safety layer manages present and future pump commands based on past and present pump commands in excess of the saturation limits, such that the modified pump command never exceeds this limit. The controller output safety layer can be thought of as a buffer of the pump command such that at any given time, saturation doesn't occur, and that only any necessary portion of the remaining command is to be delivered in the future, and that these necessary portions are to be delivered in the manner such that the system will respond in a stable and preferred manner in the context of feedback control design.

Concurrent with the controller output safety layer's role of buffering the pump command, the CGM data being sent to the controller must be modified such that the temporal discrepancy observed between the actual CGM output and the controller's estimate of the sensor due to saturation constraints will not cause the controller to generate a counter-productive correction. The common elements between the controller output safety layer and the controller input safety layer then ensures that the controller input safety layer prevents undesired feedback coupling associated with excessive commands from further degrading the system, and modifies the CGM data so that the controller will discount the effect of saturation that the controller output safety layer has already considered.

In one exemplary illustration, the safety layer module (comprising linear conditioning) interface between components keeps track of commands in the overall system. In an embodiment in which the safety layer module interface is integrated with medical device 30, 32, this is accomplished by writing and reading to memory 40. An older, or third party, insulin pump may have a maximum delivery rate of, for example, one (1) unit per time period n. However, the controller module may determine by way of the sensor or method described herein that the user requires an adjusted delivery of three (3) units. The control output safety layer intercepts the pump command from the controller module and calculates a delivery schedule according to the pump requirements. In this instance, the controller module may be further programmed for a pump having a maximum limit of two (2) units. The controller module will then divide the units accordingly, for example, a first delivery of two (2) units followed by a pending second delivery of one (1) unit at a later time (assuming no other change in conditions). The safety layer will intercept the first delivery to enforce the actual pump rate limit. The memory 40 keeps track of all deliveries and the time of such deliveries so that processor 33 can properly calculate a further delivery schedule, with the possibility of a tapered delivery to more safely deliver the needed medication to the user, whose delivery trajectory will not excite any system dynamics. The safety layer, knowing that the controller module is programmed for a maximum delivery of two (2) units and the pump is programmed to accept a maximum delivery of one (1) unit, generates a delivery of one (1) unit. In this manner, there is one (1) undelivered unit and one (1) pending unit. The processor can read the memory and determine that one (1) pending unit was not delivered at this instant. At the next time step (t=0+n), assuming the controller module attempts to follow-through on the initial plan, the controller module delivers a request for one (1) unit which it had planned to deliver for this time step. The safety layer then counts a total of two (2) units requested, and ensures a maximum of one (1) unit is commanded to the pump. At the next time step (t=0+2n), if the controller module does not send any other request, the safety layer then will choose to taper the delivery of the remaining one (1) unit according to a model-based user profile or other preprogrammed delivery profile or input. The safety layer may then deliver 0.8 units at t=0+2n and another 0.2 units at t=0+3n. In one embodiment, when the safety layer has safely delivered the medication to the delivery device the system will again store a final reading along with all data delivery points and proceed to reset for the next delivery. These stored constants and/or variables may be a factor in the next delivery schedule. In an embodiment in which the safety layer module interface resides on electronic device 12 or remote device 50, 52, the components therein (for example, memory, processor, I/O) may be employed in the same or similar manner as, or in connection with, an embodiment using components of medical device 30, 32.

There are other nonlinear control architecture and synthesis theories that can be used to serve the same role, and the general concept remains the same. One embodiment uses a control theory and architecture that deals with bounded input, state, or output systems in order to create a modular artificial pancreas platform. Thus, one aspect of the depicted embodiments allows for outside-designed controllers and/or other components to be as modular as possible with respect to limit-related hazards.

The foregoing descriptions for the preferred embodiments have been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

Thus, it can be seen that present invention provides a safety layer for use in a closed loop or semi-closed loop integrated diabetes management (IDM) system that provides modularity for rapid development of system components by different designers, and bestows an increased sense of freedom to the user, such as the ability to self-medicate in conjunction with a closed-loop system, all while providing for safety in the accurate delivery of insulin. In one aspect, the safety layer of the present invention provides a tradeoff between system safety and perceived system flexibility. In another aspect, the safety layer further envelops critical components of an IDM system to maximize the modularity of system components with respect to value constraints that can change due to component hardware and software upgrades over the life of the system. Practically, this means that as new components are being introduced in place of older ones, new constraints and new values of existing constraints will not render an existing controller obsolete and in dire need for a redesign. Moreover, integrating such a safety layer with a CGM sensor and a pump, allows rapid controller development by outside hardware and/or software designers. Overall, the safety layer provides an abstraction layer between the maintained components and outside designed components to greatly increase the robustness of the overall system.

Although the present invention has been described in detail with regard to the preferred embodiments and drawings thereof, it should be apparent to those of ordinary skill in the art that various adaptations and modifications of the present invention may be accomplished without departing from the spirit and the scope of the invention. Accordingly, it is to be understood that the detailed description and the accompanying drawings as set forth hereinabove are not intended to limit the breadth of the present invention.

What is claimed is:

1. An integrated diabetes management system, comprising:
   a glucose sensor configured to provide sensor glucose data representative of sensed glucose;
   a delivery device configured to deliver medication in response to a delivery control signal;
   a controller programmed to receive the sensor glucose data and to provide a first output control signal as a function of the received sensor glucose data; and
   a safety layer programmed to receive the first output control signal, to modify the received first output control signal to generate a second output control signal that is a modified version of the first output control signal, and to provide the second output control signal as the delivery control signal.

2. The integrated diabetes management system of claim 1, wherein the safety layer is further programmed to monitor an amount of medication delivered and to modify the received first output control signal at least partially as a function of the monitored amount of medication delivered.

3. The integrated diabetes management system of claim 2, wherein the monitored amount of medication delivered comprises insulin on board.

4. The integrated diabetes management system of claim 1, wherein the safety layer is further programmed to modify the received first output control signal in accordance with a characteristic of at least one of the glucose sensor and the delivery device.

5. The integrated diabetes management system of claim 1, wherein the safety layer is further programmed to modify the received first output control signal as a function of delivery device output.

6. The integrated diabetes management system of claim 1, further comprising: a communication module;
   wherein the controller comprises a controller calculation software module configured to provide the first output control signal;
   wherein the communication module is configured to provide the delivery control signal to the delivery device; and
   wherein the safety layer is further programmed to intercept the received first output control signal and substitute the received first output control signal with the second output control signal without any reconfiguration of the communication module or the controller calculation software module.

7. The integrated diabetes management system of claim 1, wherein: the controller comprises a controller calculation software module configured to receive the sensor glucose data; and
   the safety layer is further programmed to intercept the received sensor glucose data from the glucose sensor and cause the modified sensor glucose data instead of the received sensor glucose data to be provided to the controller calculation software module without any reconfiguration of the glucose sensor or the controller calculation software module.

8. The integrated diabetes management system of claim 1, wherein the safety layer is further programmed to:
   determine a maximum medication delivery rate of the delivery device;
   determine an amount of medication the first output control signal is configured to cause to be delivered; and
   generate, if the first output control signal is configured to cause the delivery device to deliver medication at a higher medication delivery rate than the maximum medication delivery rate of the delivery device, the second output control signal such that the second output control is configured to cause the amount of medication to be delivered according to a modified medication delivery rate that does not exceed the maximum delivery rate of the delivery device.

9. The integrated diabetes management system of claim 8, further comprising a visual display,
   wherein the safety layer is further programmed to cause the modified medication delivery rate to be displayed on the visual display.

10. The integrated diabetes management system of claim 1, wherein:
    the glucose sensor includes an output having a first range representative of glucose levels;
    the controller has an input having a second range representative of glucose levels;
    the second range is different from the first range; and
    the safety layer is further programmed to receive the sensor glucose data from the glucose sensor, modify the received sensor glucose data for compatibility with the second range, and cause the modified sensor glucose data to be provided to the input of the controller.

11. The integrated diabetes management system of claim 1, wherein:
    the glucose sensor is configured to provide sensor glucose data having a first format; and
    the safety layer is further programmed to:
      determine if the first format is equivalent to a second format; and
      modify, if the first and second data formats are not equivalent, the sensor glucose data having the first format to have the second format, wherein the controller is configured to receive the sensor glucose data having the second format instead of the first format.

12. The integrated diabetes management system of claim 1, wherein the safety layer further comprises:
    an input safety module operably connected to the glucose sensor; and
    an output safety module operably connected to the delivery device.

13. The integrated diabetes management system of claim 12, wherein the output safety module provides feedback to the input safety module.

14. A method of diabetes management, comprising:
    sensing glucose and providing sensor glucose data representative of sensed glucose;
    delivering medication in response to a delivery control signal;

receiving the sensor glucose data and providing a first output control signal as a function of the received sensor glucose data;

modifying the received first output control signal to generate a second output control signal that is a modified version of the first output control signal; and providing the second output control signal as the delivery control signal.

15. The method of diabetes management of claim 14, further comprising:

intercepting the received first output control signal; and substituting the received first output control signal with the second output control signal.

16. The method of diabetes management of claim 14, further comprising:

safety monitoring the received sensor glucose data between the steps of receiving the sensor glucose data and providing the received first output control signal; and separately safety monitoring the received first output control signal.

17. The method of diabetes management of claim 16, wherein the step of separately safety monitoring the received first output control signal comprises providing feedback.

18. The method of diabetes management of claim 17, wherein the step of providing feedback comprises providing feedback as a function of a limit on the delivery of medication and the second output control signal; and further comprising modifying the received sensor glucose data at least partially as a function of the feedback.

19. The integrated diabetes management system of claim 1, wherein the safety layer is further programmed to modify the received sensor glucose data to generate modified sensor glucose data.

20. The integrated diabetes management system of claim 1, wherein the safety layer comprises linear conditioning.

* * * * *